US006208788B1

(12) United States Patent
Nosov

(10) Patent No.: US 6,208,788 B1
(45) Date of Patent: Mar. 27, 2001

(54) APPARATUS AND METHODS FOR CONCENTRATING LIGHT THROUGH FIBER OPTIC FUNNELS COUPLED TO DENTAL LIGHT GUIDES

(75) Inventor: Vassiliy Nosov, Klyazminskaya ulitsa (RU)

(73) Assignee: Ultradent Products, Inc., Sandy, UT (US)

( * ) Notice: Subject to any disclaimer, the term of this patent is extended or adjusted under 35 U.S.C. 154(b) by 0 days.

(21) Appl. No.: 09/124,101

(22) Filed: Jul. 29, 1998

(51) Int. Cl.[7] ............... G02B 6/04; A61C 1/00; A61B 18/18; F21V 5/04
(52) U.S. Cl. .............. 385/121; 385/115; 385/134; 433/29; 606/15; 606/17; 607/93; 362/554; 362/572; 362/573
(58) Field of Search .................... 362/573, 574, 362/572, 554; 433/29, 215; 606/2, 13, 14, 15, 17; 385/115, 116, 121, 125, 134; 156/418, 656; 607/93

(56) References Cited

U.S. PATENT DOCUMENTS

| | | | |
|---|---|---|---|
| 3,590,232 | * 6/1971 | Sadowski | 362/573 |
| 3,834,391 | * 9/1974 | Block | 385/115 |
| 4,460,337 | * 7/1984 | Landgraf et al. | 433/29 |
| 4,519,780 | * 5/1985 | Strohmaier et al. | 433/29 |
| 4,597,030 | * 6/1986 | Brody et al. | 362/572 |
| 4,666,405 | 5/1987 | Ericson | 433/229 |
| 4,666,406 | 5/1987 | Kanca, III | 433/229 |
| 4,693,244 | * 9/1987 | Daikuzono | |
| 4,736,743 | * 4/1988 | Daikuzono | |
| 4,849,859 | * 7/1989 | Nagasawa | 385/134 |
| 4,875,754 | * 10/1989 | Rao et al. | |
| 5,030,093 | 7/1991 | Mitnick | 433/164 |
| 5,071,222 | * 12/1991 | Laakmann et al. | 385/134 |
| 5,139,495 | * 8/1992 | Daikuzono | 606/17 |
| 5,326,263 | * 7/1994 | Weissman | 433/224 |
| 5,346,489 | * 9/1994 | Levy et al. | 606/15 |
| 5,348,552 | * 9/1994 | Kakajima et al. | 606/16 |
| 5,371,826 | 12/1994 | Friedman | 385/115 |
| 5,587,284 | * 12/1996 | Brattesani | 433/29 |
| 5,664,042 | * 9/1997 | Kennedy | 385/134 |
| 5,825,958 | * 10/1998 | Gollihar et al. | 385/125 |
| 5,971,755 | * 10/1999 | Liebermann et al. | 606/17 |
| 6,104,853 | * 8/2000 | Mikyagi et al. | 385/125 |
| 6,110,167 | * 8/2000 | Cozean et al. | 606/17 |
| 6,129,721 | * 10/2000 | Kataoka et al. | 606/16 |

FOREIGN PATENT DOCUMENTS

1026208 * 4/1966 (GB) ................. 385/115

* cited by examiner

Primary Examiner—Cassandra Spyrou
Assistant Examiner—John Juba, Jr.
(74) Attorney, Agent, or Firm—Workman, Nydegger & Seeley

(57) ABSTRACT

Apparatus and methods for light activation of hardenable materials, such as filling materials located on dental surfaces, through fiber optic funnels coupled to light guides. Light generated by a light unit is directed through a light guide and then concentrated by a fiber optic funnel to direct concentrated light to hardenable materials. The fiber optic funnels comprises bundles of fiber optic strands. The fiber optic funnels are able to concentrate light according to their respective tapers. The fiber optic funnels are coupled to light guides by couplers which can be either rigid or elastomeric such that the couplers can be coupled with a specific light guide or conform to light guides having different diameters. A coupler can also enable a fiber optic funnel to pivot.

57 Claims, 13 Drawing Sheets

APPARATUS AND METHODS FOR CONCENTRATING LIGHT THROUGH FIBER OPTIC FUNNELS COUPLED TO DENTAL LIGHT GUIDES

BACKGROUND OF THE INVENTION

1. The Field of the Invention

The present invention relates to apparatus and methods for light activation of hardening material. More particularly, the present invention is directed to apparatus and methods for activating dental compositions on a person's teeth. The apparatus and methods for activating dental compositions utilize a fiber optic funnel configured to focus radiant energy on a tooth of a person being treated.

2. Relevant Technology

Hardenable materials which are activated by radiant energy are commonly used in dentistry as sealants, adhesives and as filling material in dental preparations. Such hardenable materials are typically activated by exposure to radiant energy in a preselected spectral range, typically in either the long-wave ultraviolet light or blue visible spectrum. The light utilized to activate the hardenable material, or more specifically the photocurable material, is typically tailored specifically to the type of material.

A light curing unit containing a reflector lamp is used to irridate the photocurable material by directing light from the reflector lamp through a light guide positioned with its distal end adjacent to the photocurable material to be cured. The light guide functions to channel the light to the material located on a dental substrate during a dental procedure.

FIG. 1 schematically depicts a source of light 10 as utilized in a conventional light curing unit and light guide. FIG. 1 corresponds with FIG. 1 of U.S. Pat. No. 5,371,826, which is incorporated herein by reference. The source of light comprises a lamp filament 12 and a parabolic reflector 11; the light source is an example of means for generating light and then providing light to a light guide. The lamp filament 12 is disposed on the optic axis 13 within the light source 10 to reflect cones of light 17 off the reflector 11 toward a focal spot where light guide 15 is positioned. Light guide 15 has a light-receiving surface 14 oriented perpendicular to the optic axis 13 to receive the incident cones of light 17. The cones of light 17 are received at an acceptance angle which for maximum efficiency, should be as large as possible. The mathematical sine of the maximum acceptance angle, known as the numerical aperture, is determined by the optical properties of the fiber optic material and its shape The diameter of the light guide 15 at the light-receiving surface 14 is selected to maximize the efficient collection of light incident at the focal plane, coinciding with the light-receiving surface 14, and is generally in a range of between 8–13 mm. It is conventional for light guide 15 to have a curved end section 16 to satisfy the requirements of maneuverability and accessibility of the light guide 15 for placement in the oral cavity of a dental patient. The curved section 16 has a radius of curvature which is chosen in proportion to the diameter of the curved end of the light guide 15, with an angle of curvature of from, thirty degrees (30°) to sixty degrees (60°), for a diameter range of between about 8 mm to about 16 mm.

Conventional light guides are generally either fiber optic conductors or are solid conductors formed from glass or plastic. Light guides formed with fiber optics typically contain multiple strands of glass fiber held together as a flexible bundle or as a solid rod of fused individual fibers.

The use of such light guides with light curing units enables a dental practioner to rapidly harden compositions such that many dental procedures can be efficiently completed. It is often difficult, however, to direct sufficient light to only a small specific area without also directing light to areas which preferably do not receive any radiant energy. Many conventional light guides have diameters of about 11 mm or about 8 mm which is often larger than a typical dental preparation. Accordingly, smaller diameter light guides, such as those having diameters of about 2 mm, are also available. However, using light guides with smaller diameters also results in less light being delivered to the photocurable material. Additionally, the need for light guides with different diameters increases the costs of dental procedures.

An attempt to overcome the problems associated with delivering an optimal amount of light to relatively small areas is disclosed in U.S. Pat. No. 5,371,826. U.S. Pat. No. 5,371,826 discloses a fiber optic light guide which is tapered for concentrated delivery of light. More specifically, the fiber optic strands bundled together in the light guide each have a taper such that the diameter of the guide is less at the distal end than it is at the proximal end. To form such a tapered light guide, each fiber optic strand may be separately tapered, bundled and then fused together or a length of solid fiber optic may be stretched to form an elongated stretched section of conical geometry wherein each strand is uniformly tapered over the stretched section.

While the tapered light guide disclosed in U.S. Pat. No. 5,371,826 may be useful to deliver more light to a smaller area than is possible with conventional light guides, the tapered light guide only minimizes the problems associated with activating photocurable materials on dental substrates. Although the distal end has a diameter that enhances the ability of the light guide to be placed into smaller openings, it is still inadequate for some uses such as in a deep and narrow preparation. As indicated at column 3, line 64 to column 4, line 13, the taper angle is preferably relatively small to minimize the loss of light due to the angle of incidence becoming smaller than the critical angle. Claim 3 indicates that the taper angle for each fiber optic strand is preferably less than 0.1° and that the taper angle of the light guide is less than 5°. Accordingly, the diameter at the distal end of the light guide is not significantly less than the diameter at the proximal end of the light guide. Additionally, while the tapered light guide increases the concentration of the light delivered to a particular surface area as compared to conventional light guides, it is preferably to have even greater concentration in some circumstances than such slight tapers can deliver. Further, such tapered light guides fail to eliminate the need for multiple light guides having different diameters.

Such tapered light guides deliver large amounts of light compared to similarly sized light guides, however, such claims are primarily supported when the amount of light delivered is measured as the amount coming out of the distal end of the light guides. Even though a tapered light guide delivers more concentrated light, the light still tends to flare outward such that the diameter of the area that receives the light is much greater than the diameter of the distal end of the light guide. In clinical use, the distal end of the light guide is typically offset from the target photocurable material at a distance which produces flaring. Accordingly, the amount of light delivered to the target area is substantially less than amount of light exiting the distal end of the light guide. Comparative measurements taken to determine the amount of light delivered when the distal end of a light guide is offset from the target by about 1 cm indicate that the amount of light delivered by conventional light guides is not significantly different from supposedly more powerful light guides. Additionally, the flaring effect may also result in heat being potentially transferred to surfaces which are not intended to be targeted.

One method of reducing the offset distance between a distal end of a conventional light guide and the target photocurable material is the use of light tips attached to a light guide as disclosed in U.S. Pat. No. 4,666,405, which is incorporated herein by reference. The light tip has one end which is cone-shaped and the other end is configured for coupling with the distal end of a light guide. FIGS. 2–5 depict light tips as disclosed in U.S. Pat. No. 4,666,405.

FIG. 2 depicts a conventional light curing unit 30 connected to the proximal end or reception end 42 of a light guide 40. A light tip 50 as disclosed in U.S. Pat. No. 4,666,405 is coupled onto the distal end or transmission end 44 of light guide 50. FIG. 3 is an enlarged perspective view of light tip 50, which shows it in greater detail. Coupling portion 52 of light tip 50 is integral with cone portion 54. Cone portion 54 terminates at an apex 56. Conventional light curing units such as the unit shown at 10 typically house the elements set forth above as comprising source of light 10. Light curing unit 10 is another example of means for generating light and then providing light to a light guide.

FIG. 4 depicts cone portion 54 of light tip 50 pressed into photocurable material 60 which minimizes the offset distance between the distal end 44 of the light guide 40. Cone portion 54 is also shown being simultaneously pressed against a relatively resilient matrix band 62 which is being utilized to contain material 60. By pressing cone portion 54 of light tip 50 against matrix band 62 and into material 60 while triggering the light, the tendency of the matrix band to contract due to the shrinkage effect of the polymerized material is minimized. As a result, when matrix band 62 is pushed to the proximal surface of the adjacent tooth 66, the space between tooth 64 and 66 has the desired dimensions. The procedure is then repeated as needed for each incremental layer. FIG. 5 depicts a tip 70 which is similar to tip 50 shown in FIGS. 2–5 except apex 76 of cone portion 74 is flattened to enhance the ability to push against a matrix band.

The tips disclosed in U.S. Pat. No. 4,666,405 are adapted to being pushed into a filing material as the tips are plastic. The use of plastic enables the tips to be inserted into the photocurable material with minimal adhesion of the material to the tip. Accordingly, the plastic tips can be reused. Additionally, even if it is necessary to discard the tips, the plastic tips are relatively in expensive as indicated at column 1, lines 54–56.

Forming tips from plastic, however, inherently limits the number of times that the tips can be utilized. After the plastic tips are inserted into photocurable material, the tips are autoclaved. After being used and autoclaved several times, it is eventually necessary to discard the tips. It would be preferable to utilize a tip that is formed from more durable materials than plastic.

While the use of the plastic tips disclosed in U.S. Pat. No. 4,666,405 minimizes the offset distance between the targeted photocurable material by requiring that the tip be introduced into the photocurable material, it would be preferable to increase the concentration of light delivered without necessitating the introduction of the tip into the material. The cone shape of the tip does concentrates some light at the apex of the cone portion, however, it is not significantly more than would be concentrated at that point when a plastic tip is not used. Additionally, as light rays exit the cone portion a significant portion of the light rays are reflected by the sides of the cone portion laterally away from the tip.

In view of the foregoing, it will be appreciated that what is needed in the art are apparatus and methods for concentrating the amount of light transmitted from a light guide to activate hardenable materials.

Additionally, it would be a significant advancement in the art to provide methods for hardening material which do not necessitate the insertion of the instrument into hardenable material.

It would be a further advancement in the art to provide methods for safely hardening materials located in small, narrow openings in a tooth.

There is also a need in the art to provide apparatus and methods for activating hardenable materials with an instrument that activates hardenable material at least primarily or entirely in the direction in which the instrument is pointed.

It would be yet another advancement in the art to provide apparatus and methods for activating hardenable materials with instruments that can be repeatedly used and autoclaved with impacting the usefulness of the instruments.

Such apparatus and methods for treatment of tooth surfaces are disclosed and claimed herein.

SUMMARY OF THE INVENTION

The present invention has been developed in response to the present state of the art and, in particular, in response to problems and needs that have not been fully or completely solved by currently available dental instruments for activating hardenable materials.

In view of the foregoing, it is an object of the present invention to provide apparatus and methods for concentrating the amount of light transmitted from a light guide to activate hardenable materials.

It is also an object of the invention to provide methods for hardening material which do not necessitate the insertion of the instrument into hardenable material.

It is another object of the invention to provide methods for safely hardening materials located in small, narrow openings in a tooth.

Additionally, it is an object of the invention to provide apparatus and methods for activating hardenable materials with an instrument that activates hardenable material at least primarily or entirely in the direction in which the instrument is pointed.

Finally, it is another object of the invention to provide apparatus and methods for activating hardenable materials with instruments that can be repeatedly used and autoclaved with impacting the usefulness of the instruments.

The present invention is directed to apparatus and systems for concentrating light. The apparatus or light concentration instrument essentially comprises a fiber optic funnel and a coupler for coupling the fiber optic funnel to a radiant energy guide or more specifically, a light guide. The guide is also coupled to a radiant energy source or light source from which the guide receives radiant energy or light. This configuration enables radiant energy to be directed from the radiant energy source through the guide and then through the fiber optic funnel to a hardenable or photocurable material to provide concentrated amounts of radiant energy to the hardenable material. Accordingly, radiant energy may be concentrated to initiate hardening of a hardenable composition on a tooth surface while directing the radiant energy with high accuracy.

The fiber optic funnel comprises a plurality of fiber optic strands which have been stretched to yield the desired funnel shape. The rate at which the strands have been stretched determines the configuration of the funnel and the resulting degree of concentration of light. Each fiber optic funnel has a reception end configured for coupling with a light guide and each reception end has a reception surface. Opposite the reception end is a transmission end which tapers to an apex. The apex has a smaller diameter than the reception surface and is configured for directing light to a specific portion of a tooth. The transmission end is preferably appropriately configured and of an appropriate size such that the transmission end may be inserted into dental preparations in tooth.

The apex may be either flat or conically shaped. Additionally, the fiber optic funnel may be configured such that essentially all of the light which enters the fiber optic funnel at the reception surface and is transmitted via the strands then exits the strands at the apex. Alternatively, the fiber optic funnel may be shaped such that a portion of the light exits at the apex and along the length of the transmission end of the fiber optic funnel.

In some embodiments the portions of the fiber optic funnel which do not receive or transmit light are covered with a protective sheath or coating. Additionally, the reception surface of the reception end may be coated with a material such as an antireflective material or anti-infrared coatings.

The coupler may be elastomeric such that the fiber optic funnel may be coupled with light guides having varying diameters. The coupler may also be relatively rigid such that only one particular light guide diameter may be received. The coupler may also enable the fiber optic funnel to pivot.

The fiber optic funnel may also be located within a chamber of a sheath tip which is coupled to a light guide by a coupler. Additionally, the sheath tip may also be configured with a monofiber which extends into the chamber to receive light from the apex of the fiber optic funnel and to transmit light out of the sheath tip.

These and other objects and features of the present invention will become more fully apparent from the following description and appended claims, or may be learned by the practice of the invention as set forth hereinafter.

BRIEF DESCRIPTION OF THE DRAWINGS

In order that the manner in which the above-recited and other advantages and objects of the invention are obtained, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which.

DETAILED DESCRIPTION OF THE PREFERRED EMBODIMENTS

The present invention comprises apparatus and methods for concentrating radiant energy and directing the concentrated radiant energy on to hardenable compositions. The radiant energy concentrating instrument is particularly useful in activating hardenable compositions which have been placed on biological substrates, such as dental substrates, during procedures such as filling a preparation in a tooth.

The apparatus or light concentration instrument essentially comprises a fiber optic funnel and a coupler for coupling the fiber optic funnel to a radiant energy guide or more specifically, a light guide. The guide is also coupled to a radiant energy source or light source from which the guide receives radiant energy or light. This configuration enables radiant energy to be directed from the radiant energy source through the guide and then through the fiber optic funnel to a hardenable or photocurable material to provide concentrated amounts of radiant energy to the hardenable material. Accordingly, radiant energy may be concentrated to initiate hardening of a hardenable composition on a tooth surface while directing the radiant energy with high accuracy.

As previously indicated, the present invention is particularly useful in such intraoral applications as filling a preparation in a tooth. In addition to being useful in dental procedures in a dental office, the present invention can also be used extraorally for example in a dental laboratory. Accordingly, the present invention may be used intraorally or extraorally.

Figure 1:
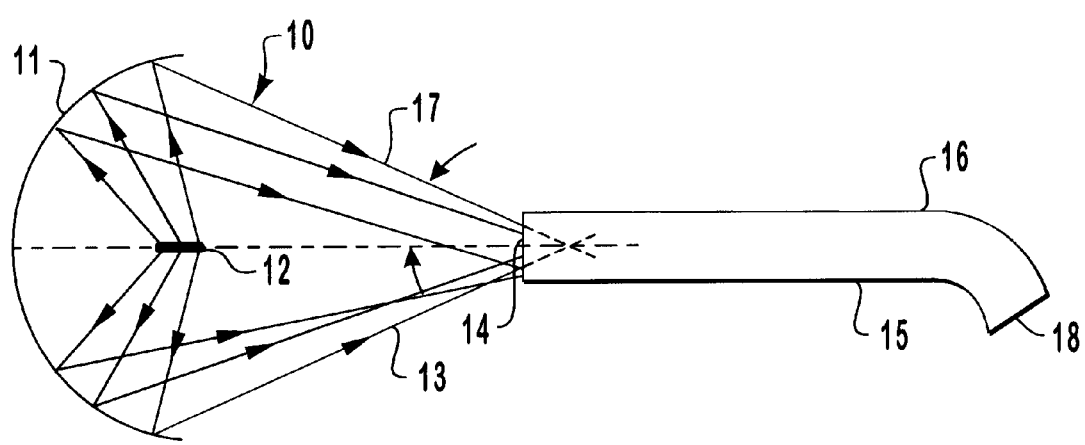
FIG. 1 is a schematic representation of a conventional light source as utilized with a conventional light guide.
Figure 2:
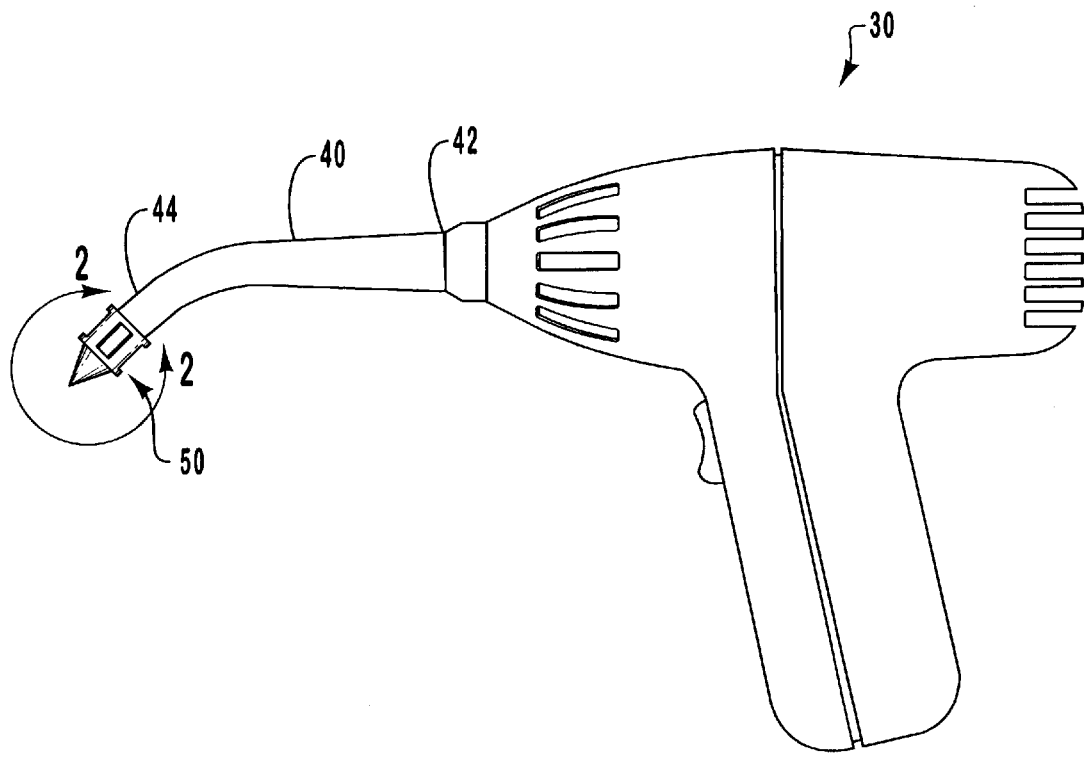
FIG. 2 is side view of a conventional light curing unit coupled to a conventional light guide with a plastic light tip attached at the transmission end of the light guide.
Figure 3:
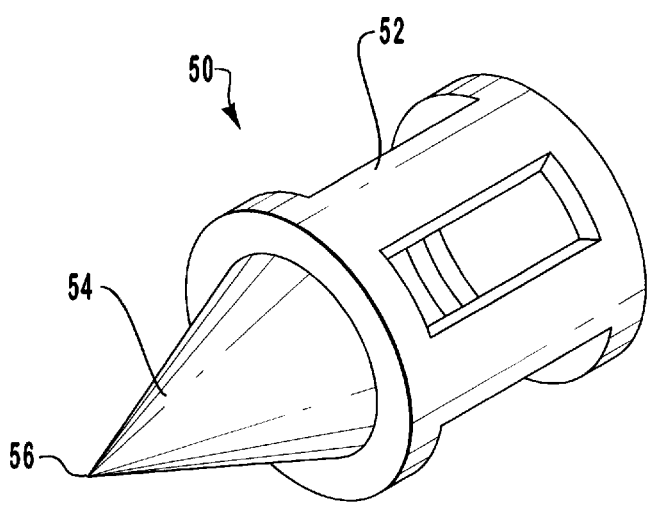
FIG. 3 is an enlarged perspective view of the conventional plastic tip shown in FIG. 2.
Figure 4:
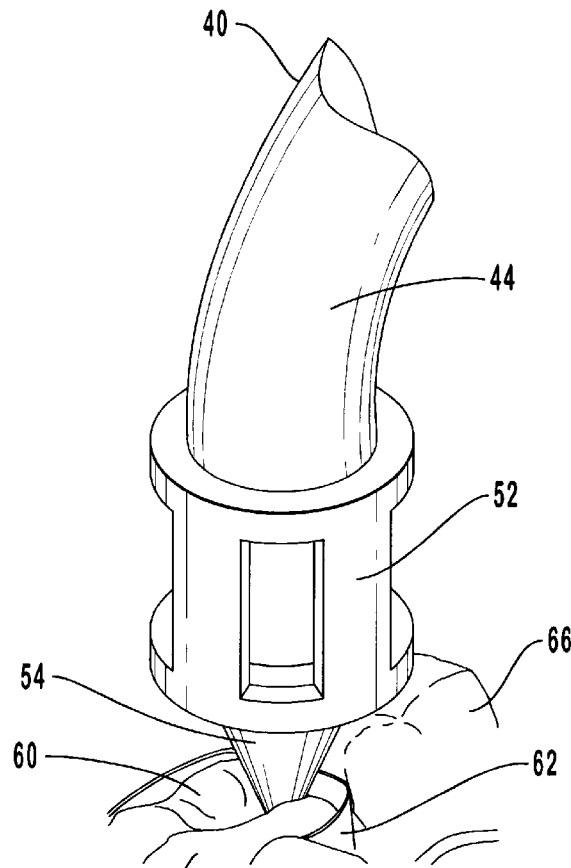
FIG. 4 is a perspective view of the plastic tip shown in FIG. 2 being pressed into hardenable material contained by a matrix band.
Figure 5:
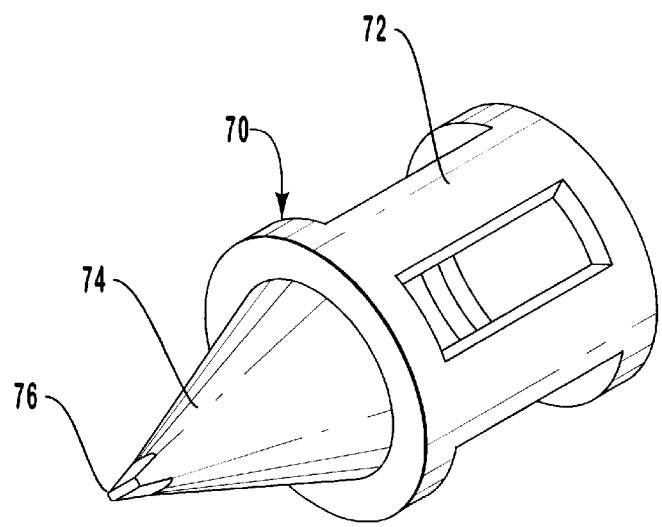
FIG. 5 is an enlarged perspective view of another embodiment of a plastic light tip.
Figure 6:
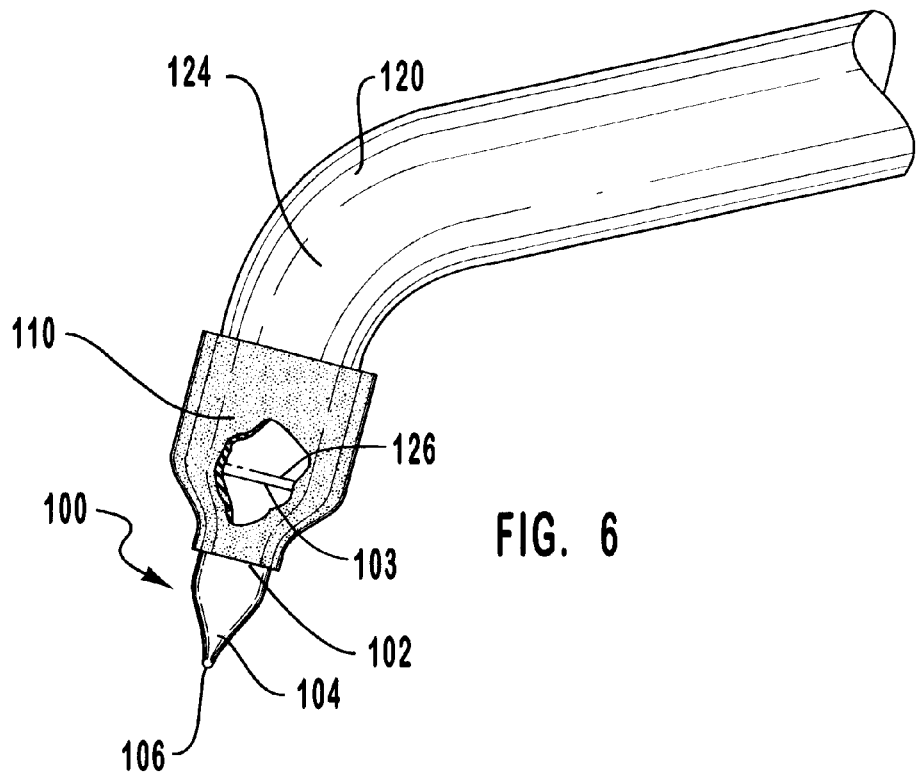
FIG. 6 is a perspective view of a fiber optic funnel and a coupler attached to a light guide with a partial cut-away view.
Figure 7:
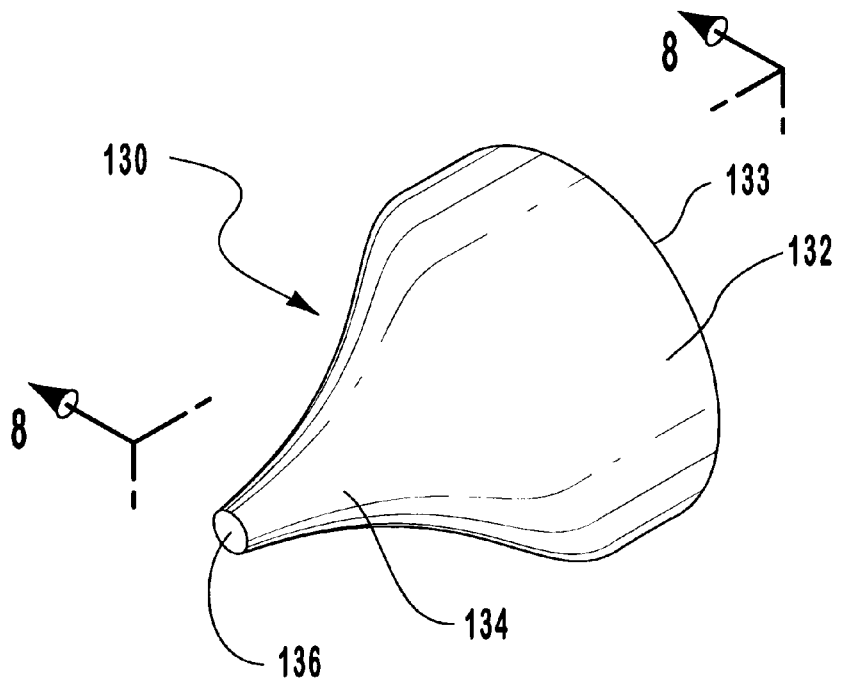
FIG. 7 is an enlarged perspective view of another embodiment of the fiber optic funnel.
Figure 8:
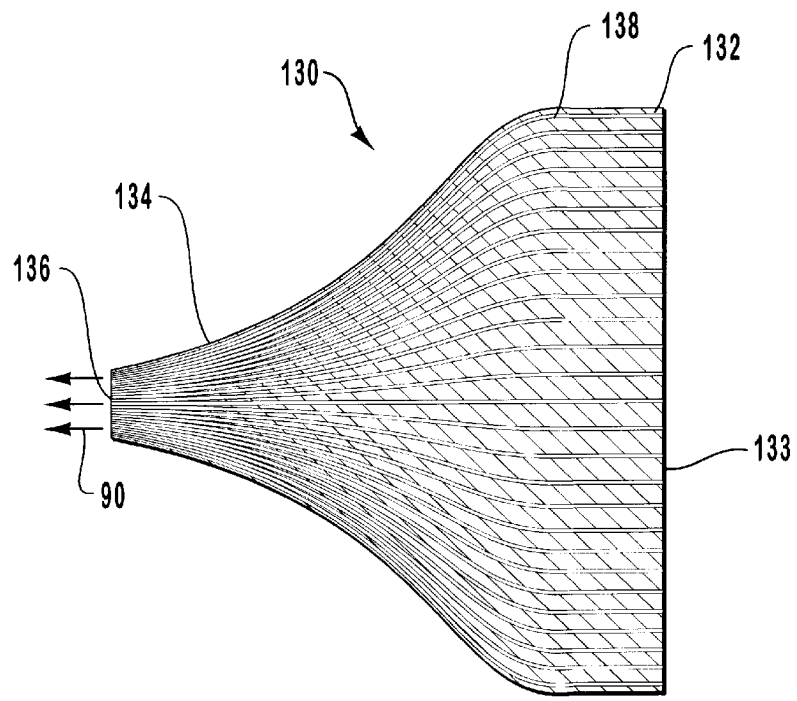
FIG. 8 is an enlarged longitudinal cross-sectional view of the fiber optic funnel depicted in FIG. 7.
Figure 9:
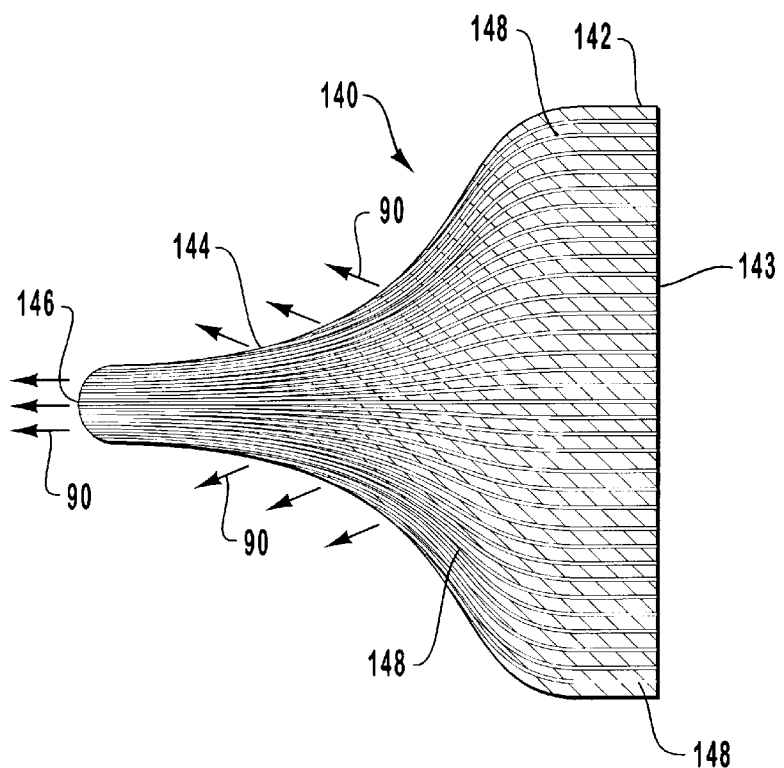
FIG. 9 is an enlarged longitudinal cross-sectional view of a fiber optic funnel ground to provide some degree of lateral transmission of light.
Figure 10:
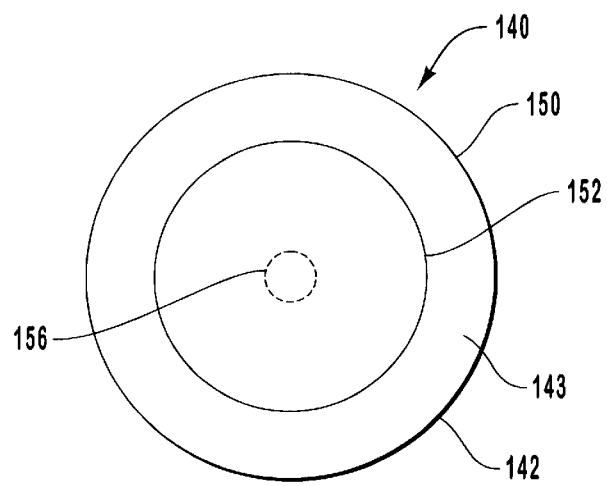
FIG. 10 is a top view of the fiber optic funnel shown in FIG. 9.
Figure 14:
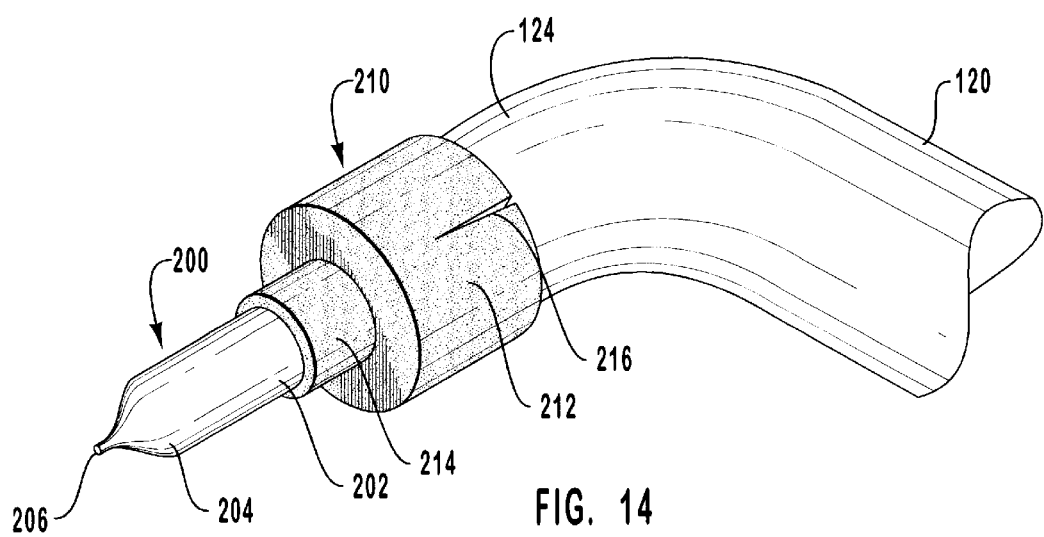
FIG. 14 is a perspective view of another embodiment of a fiber optic funnel and another embodiment of a coupler used to couple a fiber optic funnel to a light guide.
Figure 15:
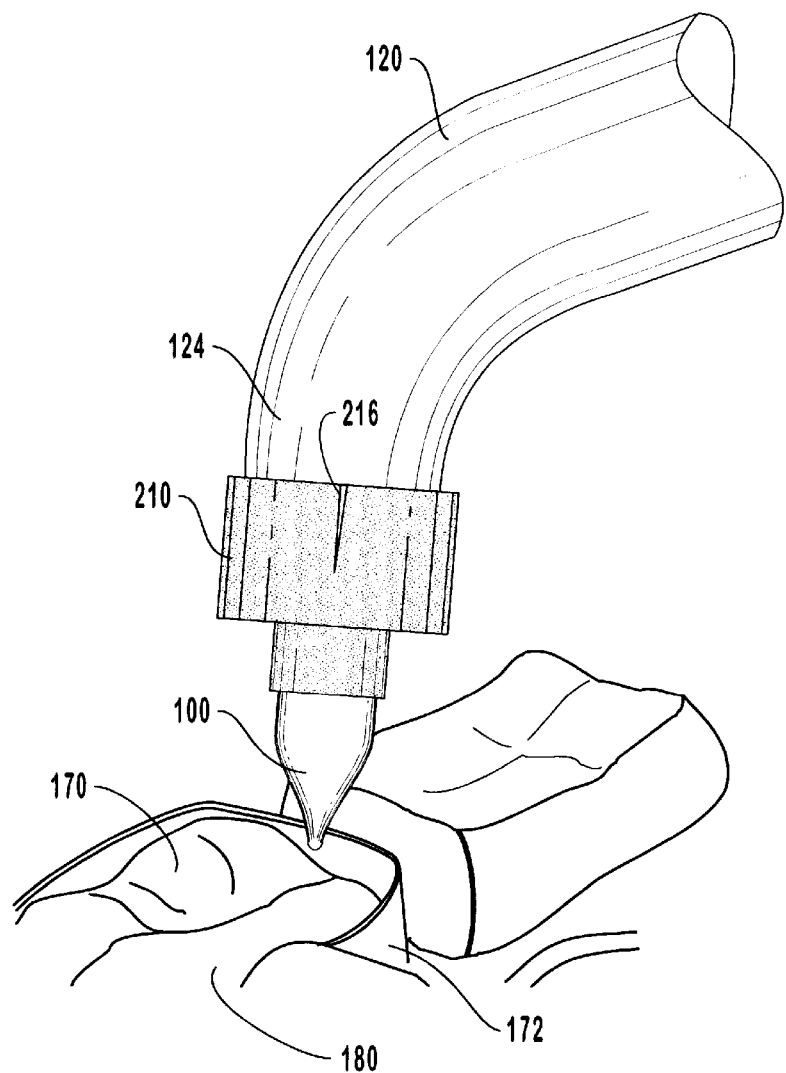
FIG. 15 is a perspective view of the fiber optic funnel shown in FIG. 6 coupled to a light guide with a coupler as shown in FIG. 14. The fiber optic funnel is activating hardenable material contained by a matrix band while being urged against the matrix band.
Figure 16:
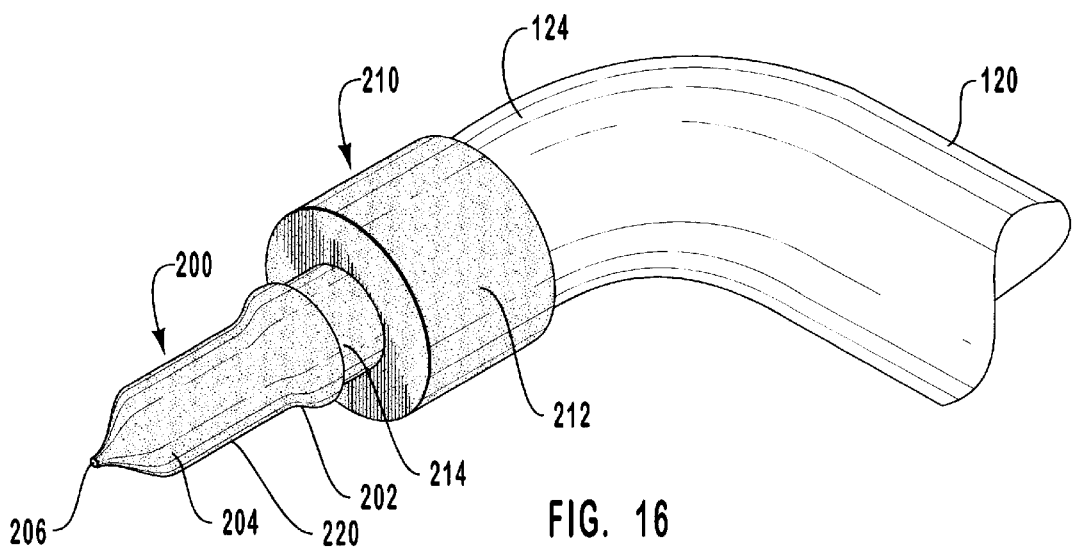
FIG. 16 is a perspective view of the fiber optic funnel shown in FIG. 14 covered by a protective sheath.
Figure 20:
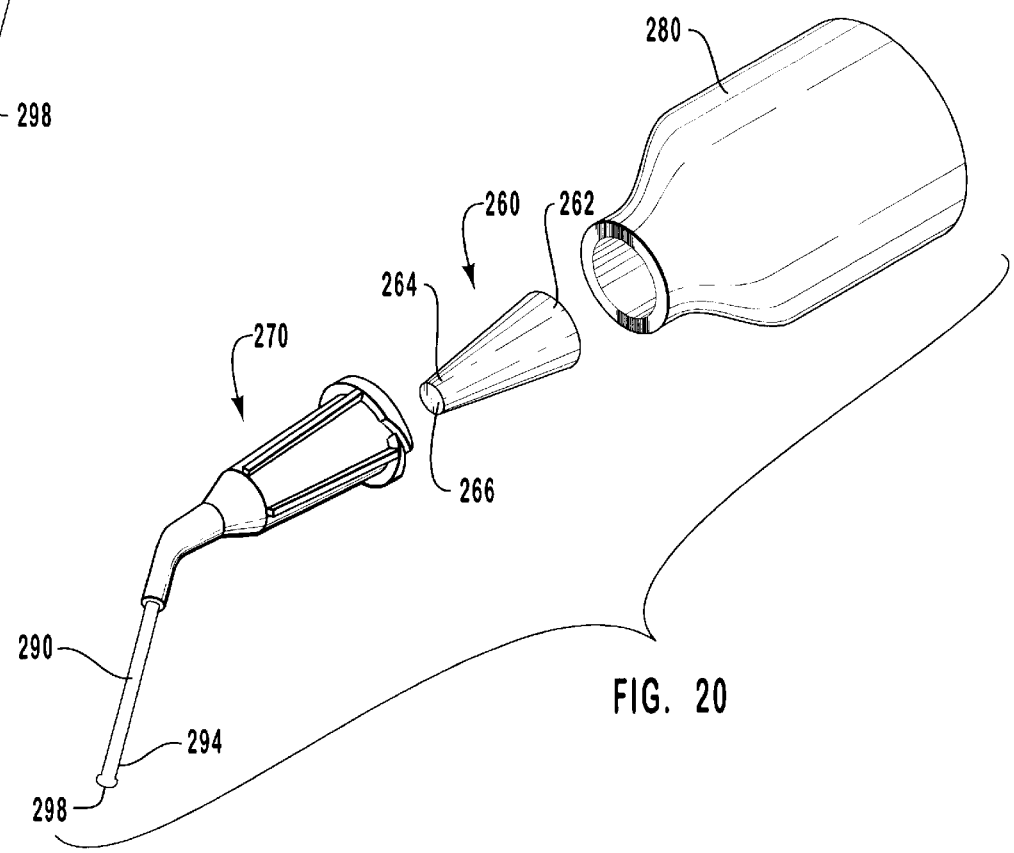
FIG. 20 is an exploded perspective view of the instrument shown in FIG. 19.
Figure 21:
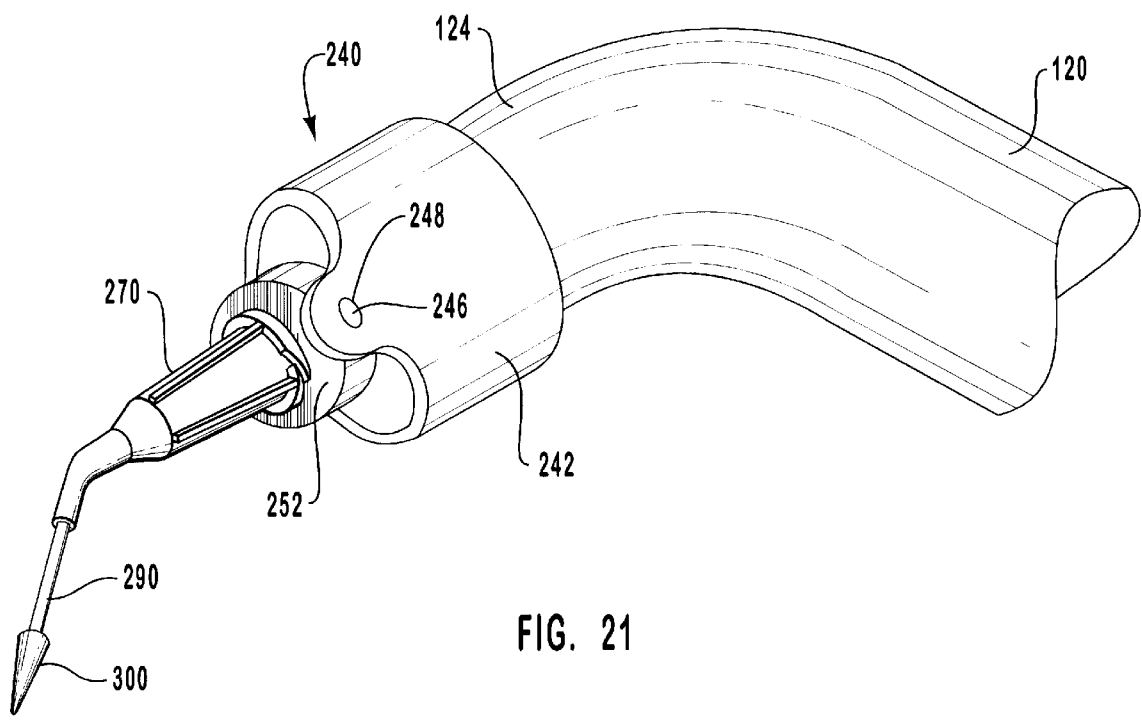
FIG. 21 is a perspective view of the sheath tip as shown in FIGS. 19 and 20 coupled to a light guide by a coupler as shown in FIGS. 17 and 18.

FIGS. 6–7 depict an embodiment of a fiber optic funnel at 100. FIG. 8 depicts a cross-sectional view of a fiber optic funnel 100. FIGS. 9–10 depict an embodiment which appears similar to fiber optic funnel 100, however the fiber optic funnel has been ground to alter the transmittance direction of the light. FIGS. 11–13 and 15 depict fiber optic funnels 100 being utilized to activate hardenable material. Another embodiment is shown in FIGS. 14 and 16 at 200. FIGS. 17–18 and 21–22 depict pivotal embodiments of the fiber optic funnel. The embodiment depicted in FIG. 18 is pivotable by a handle. FIGS. 20–22 depict embodiments wherein a fiber optic funnel is combined with a tip configured for accessing very narrow openings. Each embodiment is described in detail hereinbelow.

The radiant energy source can have any suitable configuration and can provide any radiant energy which is capable of activating hardenable material to initiate hardening of the material. The source of light 10 and a conventional light curing unit 30 which houses the elements of source of light 10 are both examples of suitable radiant energy sources or radiant energy generating means for generating radiant energy and then providing radiant energy or light to a guide. The radiant energy generating means or more specifically the light generating means is preferably configured such that it is positioned outside of the person's mouth during use. As previously indicated, the present invention may be used intraorally or extraorally which essentially enables the fiber optic funnel to be used with any radiant energy generating means. The radiant energy generating means may be any suitable light source depending on the particular use including a xenon lamp, a flash lamp, a metallohaloid lamp, infrared diodes, laser diodes, lasers, etc. Examples of preferred radiant energy generating means include conventional curing units such as the Optilux® 401 or Optilux® 501 units.

The terms "light" or "radiant energy", as used in the specification and the appended claims, refer to electromagnetic radiation. These terms include electromagnetic radiation having any wavelength with which the hardening of a hardenable composition may be activated, increased, or accelerated. Thus, these terms include, but are not limited to, electromagnetic radiation in the visible, infrared and ultraviolet regions of the electromagnetic spectrum. The light generating means preferably generates light with wavelengths concentrated, for example, within the ultraviolet region or in the blue end of the visible region of the ultraviolet spectrum.

The guide may have any suitable configuration which essentially enables a practioner to reach into and deliver radiant energy, especially light, into the oral cavity of a patient. Light guide 120 is an example of radiant energy guide means for transmitting radiant energy from a light curing unit or means for generating radiant energy. More particularly, guide 120 is an example of light guide means for transmitting light from the light generating means. Light guides 15 and 40 are also examples of such radiant energy guide means or light guide means. Light guides which transmit light by means of optical fibers are preferred although other means for transmitting light or radiant energy are acceptable. Accordingly, light guide 120 can be either a fiber optic conductor or solid conductor formed from glass or plastic. Light guides formed with fiber optics typically contain multiple strands of glass fiber held together as a flexible bundle or as a solid rod of fused individual fibers.

FIG. 6 depicts a perspective view of a fiber optic funnel 100 coupled by a coupler 110 to a distal or transmission end 124 of light guide 120. Fiber optic funnel 100 has a reception end 102 and a transmission end 104 which terminates at apex 106.

FIG. 7 depicts an enlarged perspective view of another embodiment of the fiber optic funnel at 130. Fiber optic funnel 130 has a reception end 132 with a reception surface 133. Opposite the reception end 132 of the fiber optic funnel is a conical transmission end 134 which terminates at apex 136. Apex 136 is flat while apex 106 is relatively bulbous. Flat apex 136 directs light in a straighter orientation than bulbous apex 106 which provides for some degree of lateral transmission of light. Reception surface 133 and apex 136 are preferably the only surfaces of fiber optic funnel 130 which receive or transmit light. The surfaces other than the reception surface and apex of a fiber optic funnel are referred to as the side surface of the fiber optic funnel.

The fiber optic funnel may have any suitable shape and provide any suitable amount of concentration of light. Each embodiment of a fiber optic funnel set forth herein is an example of fiber optic funnel means for concentrating radiant energy onto a hardenable material, wherein the radiant energy is received from a light generating means via a radiant energy guide means. The transmission end is preferably appropriately configured and of an appropriate size such that the transmission end may be inserted into dental preparations in a tooth. The transmission end of each fiber optic funnel tapers to an apex. The apex is preferably significantly smaller in diameter than the reception end and more particularly the reception surface. The diameter of the apex of the fiber optic funnels in the embodiments shown in the accompanying drawings are a fraction of the diameter of the respective reception surfaces. The diameters of the reception surface and the apex of the particular fiber optic funnel may have any suitable ratio depending on the intended use. Accordingly, the diameter of the apex of the fiber optic funnel may be ¾ of the diameter of the reception surface, about ½, about ¼, about ⅙, about ⅐, about ⅛, about ¹⁄₁₀ or even less than about ¹⁄₁₀ of the diameter of the reception surface.

The configuration of the fiber optic strands is shown in FIG. 8 which is a longitudinal cross-sectional view of fiber optic funnel 130. Transmission end 134 is tapered or conical as the fiber optic strands 138 have been concentrated in that portion of the funnel. The fiber optic strands are essentially all concentrated in apex of 136 such that light rays shown by arrows 90 exit fiber optic funnel essentially only from apex 136. Accordingly, the light is highly concentrated.

In prior art light activation devices, the cone of light transmitted from the device tends to significantly fan or flare, thereby reducing the intensity of the light transmitted to a point directly opposite the device. The flaring effect even impacts the overall usefulness of high powered light guides despite their high light transmittance. The farther the light guide is offset from the target, such as in deep preparations, the less light is transmitted to the target as the flaring becomes more pronounced as the offset increases. The ability to point the fiber optic funnel at a surface and then direct all of the light to the surface directly opposite the apex of the fiber optic funnel is a significant improvement. For example, high powered light guides, such as the light guide sold by Demetron under the name Turbo, deliver about 10 $mW/mm^2$ of light to hardenable compositions while coupling fiber optic funnel 100 with a light guide delivers light in a range from about 100 $mW/mm^2$ to about 150 $mW/mm^2$ as measured with an identical offset distance. While such concentration of light has many uses, it is particularly helpful in activating hardenable material located in narrow and deep preparations wherein the offset distance is greatest between the terminal end of the light transmission instrument and the hardenable composition.

Since the light is concentrated at the apex, the diameter of the area of hardenable material which receives light closely corresponds with the diameter of the apex. This enables the practioner to use the instrument with pinpoint accuracy. The fiber optic funnel ensures that radiant energy is efficiently directed at the hardenable material. Accordingly, procedures such as filling dental preparations can be completed much quicker than when using conventional instruments. Additionally, hardenable materials can be hardened without substantial irradiation of surrounding gingival tissues or other dental tissues of the person being treated. This serves to eliminate a significant portion of the discomfort that may result through the use of prior art radiant energy sources. Additionally, since the light is directed to a small area any accompanying heat quickly diffuses to surrounding tissue to minimize or eliminate any sensation.

The multiple strands of glass fibers in the fiber optic funnel are held together as a solid rod of fused individual fibers or alternatively as a relatively flexible bundle. To form such a funnel shaped portion, a length of solid fiber optic is stretched to form an elongated stretched section of conical geometry. Additionally, each fiber optic strand may be separately tapered, bundled and then fused together. It is preferable that each strand have an essentially uniform taper over the stretched section.

Methods for forming an elongated stretched section of fiber optic strands having a conical geometry are known to those skilled in the art. Essentially, a section of fiber optic strands is uniformly heated and then stretched. The rate at which the section is stretched determines the shape of the resulting cone or conical section. Generally, fast stretching yields a shorter cone with a high degree of concentration while slow stretching yields a longer cone and typically less concentration of light.

Methods for forming fiber optic components are also known to those skilled in the art. Conventional methods for forming fiber optic components are set forth in detail in the *Kirk-Othmer Concise Encyclopedia of Chemical Technology* at pages 469–470 under the heading "Fiber Optics" in the 1985 edition, which is hereby incorporated by reference. Light is transmitted through individual fibers by means of total internal reflection from the fiber walls. For efficient transmission each fiber has a highly transparent core which is usually glass that is coated with a layer of lower refractive index, usually also glass, to form a cladding. The cladding generally prevents light from leaking into neighboring fibers and protects the core.

The individual fiber strands preferably have relatively small diameters. Fiber strands having relatively small diameters are less likely to be deformed or damaged when being stretched to have a section capable of concentrating light. By using fiber strands with relatively small diameters there is less cladding material around each fiber strand and therefore less cladding material in the light guide. By minimizing the cladding material, more fiber strands can be concentrated together in the apex of the fiber optic funnel. Additionally, smaller diameters provide more openings for light rays to enter and less cladding material to reflect light.

The fiber strands can have any diameter, however, the diameter of the fiber strands is preferably in a range from about 20 microns to about 200 microns and more preferably in a range from about 35 microns to about 150 microns. The fiber optic funnel may be formed using fiber strands having either essentially the same diameters or different diameters. For example, to minimize any potential deformation from stretching fiber optic strands it may be preferable to form a fiber optic funnel with fiber optic strands having relatively small diameters, such as strands having diameters ranging from about 20 microns to about 60 microns, around a cluster of fiber optic strands located in the center having relatively large diameters, such as strands having diameters ranging from about 80 microns to about 150 microns. In such a configuration, deformation is minimized as the fiber optic strands around the perimeter which are stretched the most are more flexible than those at the center and are less likely to be deformed. Another example of a fiber optic funnel having strands with different diameters is a funnel formed with strands with smaller diameters interspersed between fiber optic strands with larger diameters to yield optimal packing of the strands.

In FIG. 6, reception end 102 is sheathed within coupler 110. The exterior surface of coupler 110 is preferably black or dark to minimize any potential for exposing the practioner's eyes to intense light. Additionally, the interior surface of coupler 110 is preferably white.

Coupler 110 is an elastomeric tube or collar. The elasticity of coupler 110 enables fiber optic funnel 100 to be connected to light guides having varying diameters. Since coupler 110 can stretch to conform to the diameter of the light guide and also to the diameter of the fiber optic funnel, any combination can be utilized. The ability to utilize combinations of varying diameters enables a practioner to deliver concentrated light into much smaller locations and in a safer manner even when the light guide has a relatively large diameter. Reception end 102 and its reception surface may have any suitable diameter, however, reception end 102 preferably has a diameter which is similar to the diameter of typical light guides. Accordingly, reception end 102 is preferably 8 mm or 12 mm.

Although the primary advantage of a fiber optic funnel is a high degree of concentration of light from the apex, it may be preferable to provide some degree of lateral transmission as is obtained with bulbous apex 106. It may be preferable, however, in some circumstances to have even greater lateral transmission of light. For example, in relatively large diameter or shallow preparations, it may be advantageous to direct light straight from the apex and also laterally away from the funnel. The embodiment shown in FIG. 9 is a cross-sectional view of a fiber optic funnel 140 which has the majority of the fiber optic strands 148 concentrated at apex 146. Light enters reception surface 143 of reception end 142 as in other embodiments, however, a portion of transmission end 144 of fiber optic funnel 140 has been ground such that some fiber optic strands 148 do not terminate at apex 146. The fiber optic strands which terminate along the length of the transmission end 144 transmit light laterally away from fiber optic funnel 140 and downward to the hardenable material. Accordingly, pointing apex 146 at hardenable material enables a practioner to direct most of the deliverable light with pinpoint accuracy while also delivering less intense light to the surrounding material.

FIG. 10 is a top view of fiber optic funnel or stated otherwise is the view seen when looking directly at reception surface 143 of reception end 142. FIG. 10 shows that the majority of the fiber strands terminate at apex 146 while the remainder terminate along the length of the transmission end 144. Perimeter 152 shown in FIG. 10 delineates the fiber optic strands 148 which terminate at apex 146, the perimeter of which is shown in phantom lines 156, from the fiber optic strands 148 which terminate along the length of the transmission end 144. Assuming that the diameter of the area defined by perimeter 150 is 10 mm and that the diameter of the area defined by perimeter 154 is 8 mm, then about 64% of the light is transmitted out of apex 146 while about 36% is transmitted along the length of transmission end 144. Such percentages may be modified by varying the concentration of the fibers, the size of the fibers or the amount of the grinding.

Figure 11:
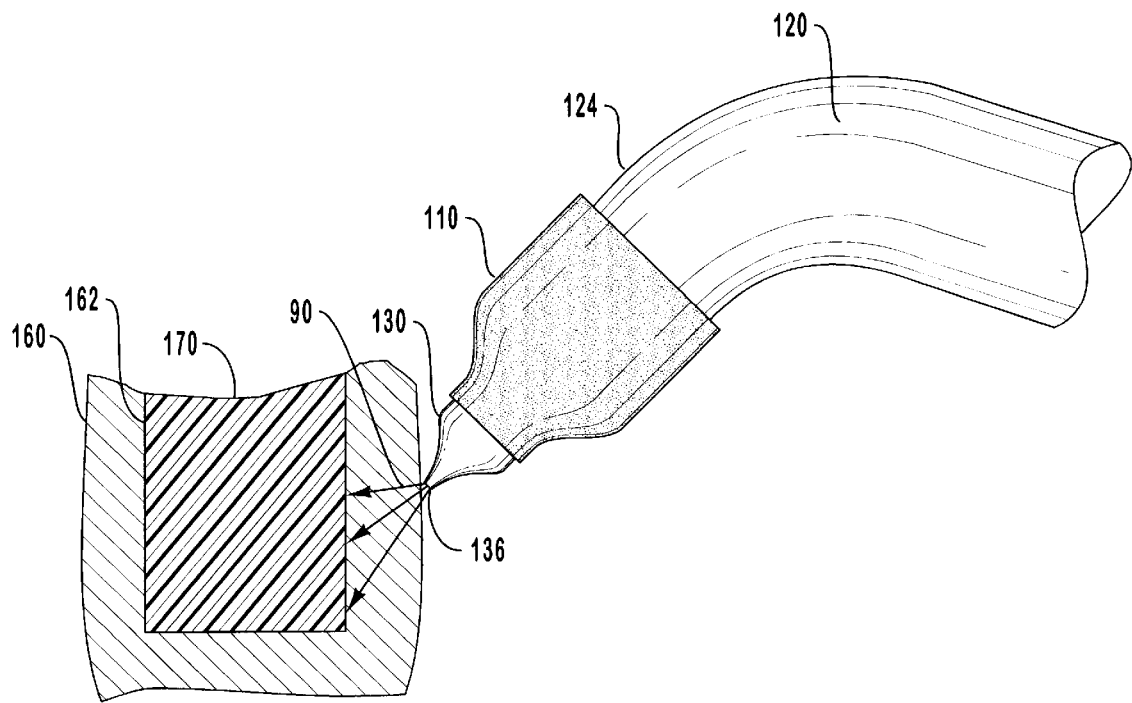
FIG. 11 is a perspective view of the fiber optic funnel depicted in FIG. 7 with a longitudinal cross-sectional view of a preparation in a tooth containing hardenable material which is being hardened by directing light through a side of the tooth.
Figure 12:
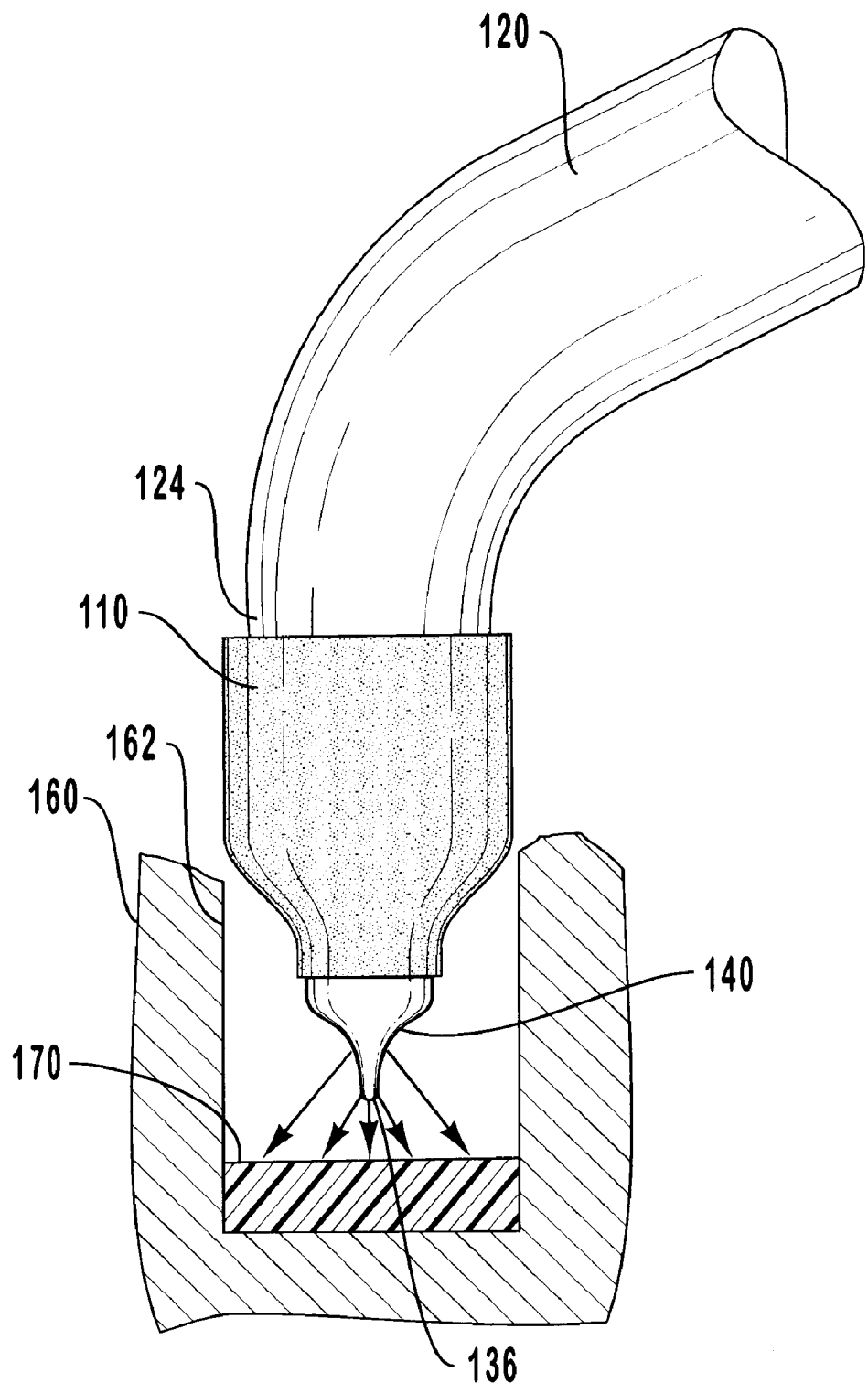
FIG. 12 is a perspective view of the fiber optic funnel depicted in FIG. 9 with a longitudinal cross-sectional view of a tooth with a preparation containing hardenable material which is being hardened by directing light into the preparation.
Figure 13:
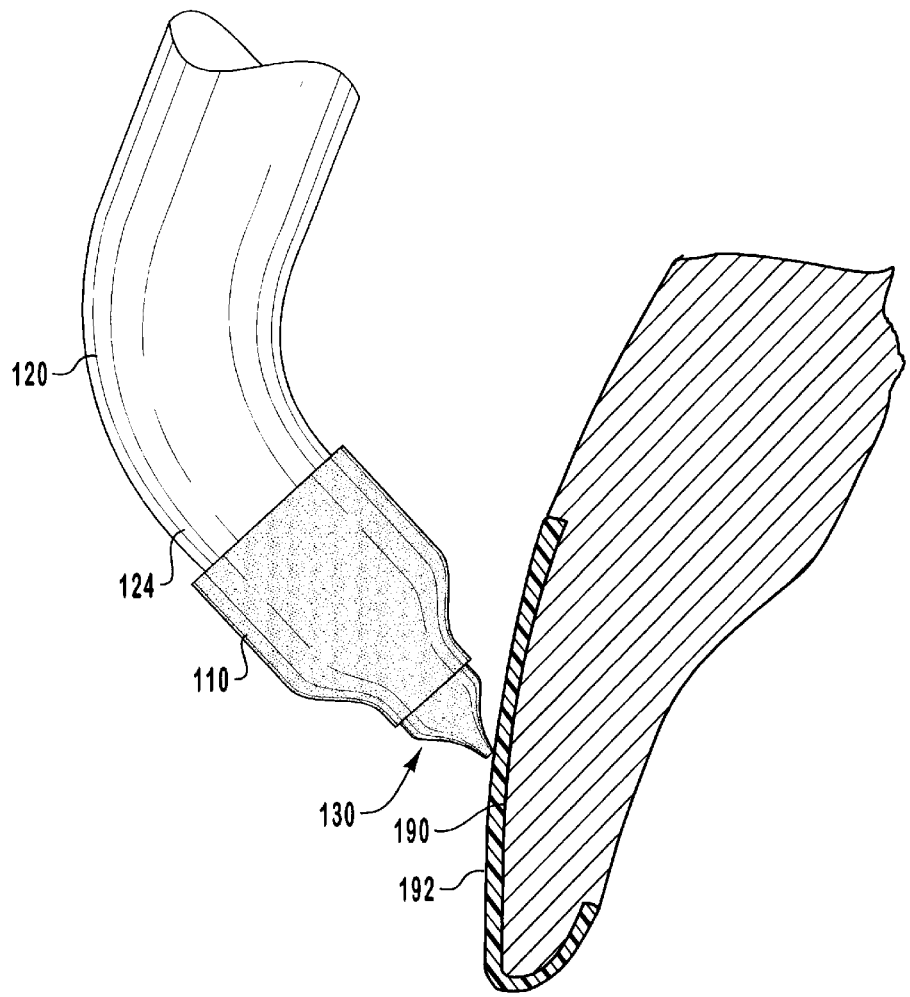
FIG. 13 is a perspective view of the fiber optic funnel depicted in FIG. 7 being utilized to secure a veneer into position on a tooth.

FIGS. 11–13 depicts some advantages of the ability of the fiber optic funnels to concentrate light. In FIG. 11, light is being transmitted from apex 136 of fiber optic funnel 100 through tooth 160 and into wall 162 of preparation to harden hardenable filling material 170. The concentration of the light is sufficiently powerful to pass through a tooth as shown in the same manner which lasers are utilized. The thickness and translucency of the tooth may, however, impact the ability of the light to pass through the tooth. A significant advantage of the ability of fiber optic funnel 130 to harden a hardenable filling material is that the polymerization is drawn toward the wall 162. Accordingly, shrinkage occurs towards the walls and the filling material is anchored into position. Since any space between material 170 and filling material is minimized or eliminated, the tooth sensitivity that is caused by such spaces is minimized or eliminated.

In addition to concentrating the light which exits the strands, into a smaller area, the taper of the transmission end enables it to access relatively narrow preparations as shown in FIG. 12. Since deep preparations are easily accessed due to the configuration of the fiber optic funnel, hardenable material 170 can be fully accessed and each layer of the hardenable material can be adequately exposed to light for complete polymerization. Another benefit of the fiber optic funnel and the coupler is that the need for very narrow light guides such as 2 mm light guides which are conventionally utilized in narrow preparations is essentially eliminated.

The fiber optic funnel and coupler are also highly useful in luting a veneer onto a tooth. As shown in FIG. 13, hardenable luting material 190 is applied and then a veneer 192 is positioned onto tooth 194. Veneer 192 is then tacked onto tooth 194 through polymerization of only a small portion of luting material 190 by holding fiber optic funnel 130 in one location as shown in FIG. 13. Then the remainder of luting material 190 may be polymerized, preferably by directing the light through the side of the tooth opposite veneer 192 to pull the hardenable material 190 to tooth 194. Light is then directed to the hardenable material 190 through veneer 192. This also avoids the need for light guides which have very small diameters.

Another embodiment of fiber optic funnel and coupler is depicted in FIG. 14. Fiber optic funnel 200 is more elongated and tapers more steeply to an apex 206 that is flat and not bulbous as is apex 106. The flatness of apex 206 enables light to be more greatly concentrated in the direction in which the apex is pointed compared with apex 106.

Coupler 210 depicted in FIG. 14 is formed from a more rigid material than coupler 110 to more securely couple fiber optic funnel 200 to transmission end 124 of light guide 120. Coupler 210 comprises a light guide end or cup 212 and a fiber optic end or cup 214. Such a coupler is preferably relatively rigid such that each respective cup can only receive a particular diameter of light guide and fiber optic funnel. However, coupler 210 is shown with a slit 216 which enables light guide cup 212 of coupler 210 to expand to fit light guides having different diameters. Coupler 210 is shown in FIG. 15 without a slit such that coupler 210 fits relatively snugly onto light guide 120. Coupler can also be formed with a light guide cup which is conical such that different diameters can be inserted and retained. Coupler 210 can also be formed from a material with sufficient elasticity to accommodate light guides with different diameters. Depending on the properties desired for the particular embodiment of the coupler, the coupler can be formed from any suitable material such as silicon resin, polyamide, epoxides, nylon, or polytetrafluoroethylene such as Teflon. Coupler 110 and coupler 210 are both examples of a coupling means for coupling the fiber optic funnel to a light guide.

FIG. 15 depicts fiber optic funnel 100 being urged against band matrix 172 which contains hardenable filling material 170. By pressing against band matrix 172 and simultaneously activating the light generating means, material 170 hardens toward band matrix 172. By enabling filling material 170 to harden toward band matrix 172, the spacing between tooth 180 and 184 is optimized. Since the force exerted by the practioner on light guide 120 must be maintained through coupler 210 to fiber optic funnel 100 as the instrument is pressed against band matrix 172, it may be preferable for the coupler to be relatively rigid.

As shown in FIG. 15, it is unnecessary to push fiber optic funnel 100 into filing material 170 as the fiber optic funnel is able to concentrate the light for pinpoint polymerization. Additionally, the fiber optic funnels are generally not adapted to being inserted into the filling material as the filling material 170 adheres onto fiber optic funnel 100, thereby potentially destroying its use. While such use may be acceptable with plastic tips as are disclosed in U.S. Pat. No. 4,666,405, the costs of the fiber optic funnels prohibits their use as a single use item. The fiber optic funnels are, however, generally very durable and can be repeatedly autoclaved without degrading the ability of the fiber optic funnels to concentrate light.

To ensure that fiber optic funnel is not contacted with filling material 170 or to at least minimize the exposure of the fiber optic funnel to filling material 170, particularly when used as shown in FIG. 15, it may be preferably to utilize a protective sheath 220. Protective sheath 220 is shown in FIG. 16 covering the entire surface of fiber optic funnel 200. However, a protective sheath may only cover a portion of the fiber optic funnel and may also be used with any type of fiber optic funnel. The protective sheath may be elastomeric or relatively rigid. Additionally, the protective sheath may cover a portion of coupler as shown in FIG. 16, may extend over the entire coupler, or may abut the coupler. In another embodiment, the portion of the fiber optic funnel which does not receive or transmit light, which in most embodiments is merely the side surface, is coated with a protective coating to enable hardenable material to be more easily removed.

Depending on the use, it may be preferable to coat the reception surface of the fiber optic funnels or the transmission surface of the light guide, such as transmission surface 126, with at least one material. For example, coating the reception surface with a filter coating which prevents or at least minimizes the transmission of electromagnetic radiation in the infrared regions of the electromagnetic spectrum can minimize the heat that is transferred to the hardenable material and tissue located within the region of the hardenable material. Examples of suitable materials include metal halides. Many anti-infrared coatings also minimize the reflectivity of the surface. Alternatively, it may be desirable to use a coating which allows only infrared light to pass through or which maximizes infrared light, for example when bleaching teeth.

Additionally, it may be useful to coat the reception surface of the fiber optic funnel or the transmission surface of a light guide with a dichroic material for diagnostic purposes such that essentially only a particular color of light, such as blue light or green light, for example, is transmitted. Similarly, the light generating means can be selected to deliver essentially only a particular color of light or portion of the light spectrum.

It may also be useful to coat the reception surface with anti-reflection coatings. Such anti-reflection coatings are particularly useful with the embodiments configured to enable the fiber optic funnel to pivot. Suitable anti-reflective materials are well known in the art and include a variety of dielectrics such as metal oxides and metal halides. An example of a conventional anti-reflection coating is a multi-layered film coating wherein layers are alternated which have high refractive index and a low refractive index. For example, when $Ta_2O_5$ is used as a material of relatively high refractive index (abbreviated as H hereinafter) and $SiO_2$ is used as material of relatively low refractive index (abbreviated as L hereinafter) the multilayer film can be illustrated as: reception surface/HLHL/air. Infrared blocking coatings, anti-reflection coatings, dichroic coatings and other desirable coatings are set forth in detail in *Optical Thin Films User's Handbook* (1987) by James D. Rancourt, which is hereby incorporated by reference.

Figure 17:
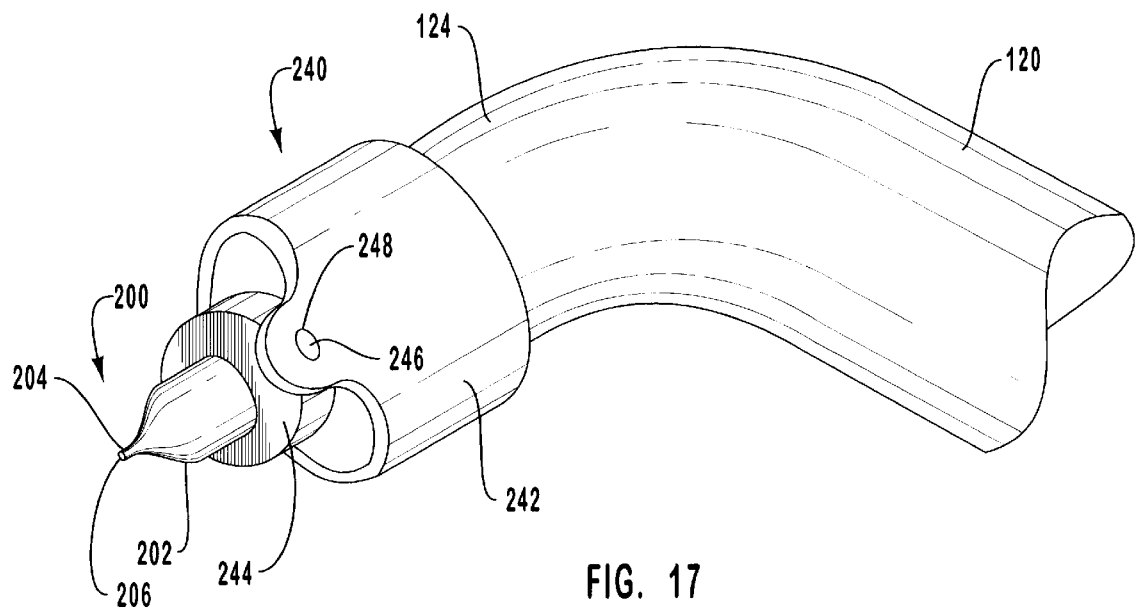
FIG. 17 is a perspective view of the fiber optic funnel shown in FIG. 14 pivotally coupled to a light guide.
Figure 18:
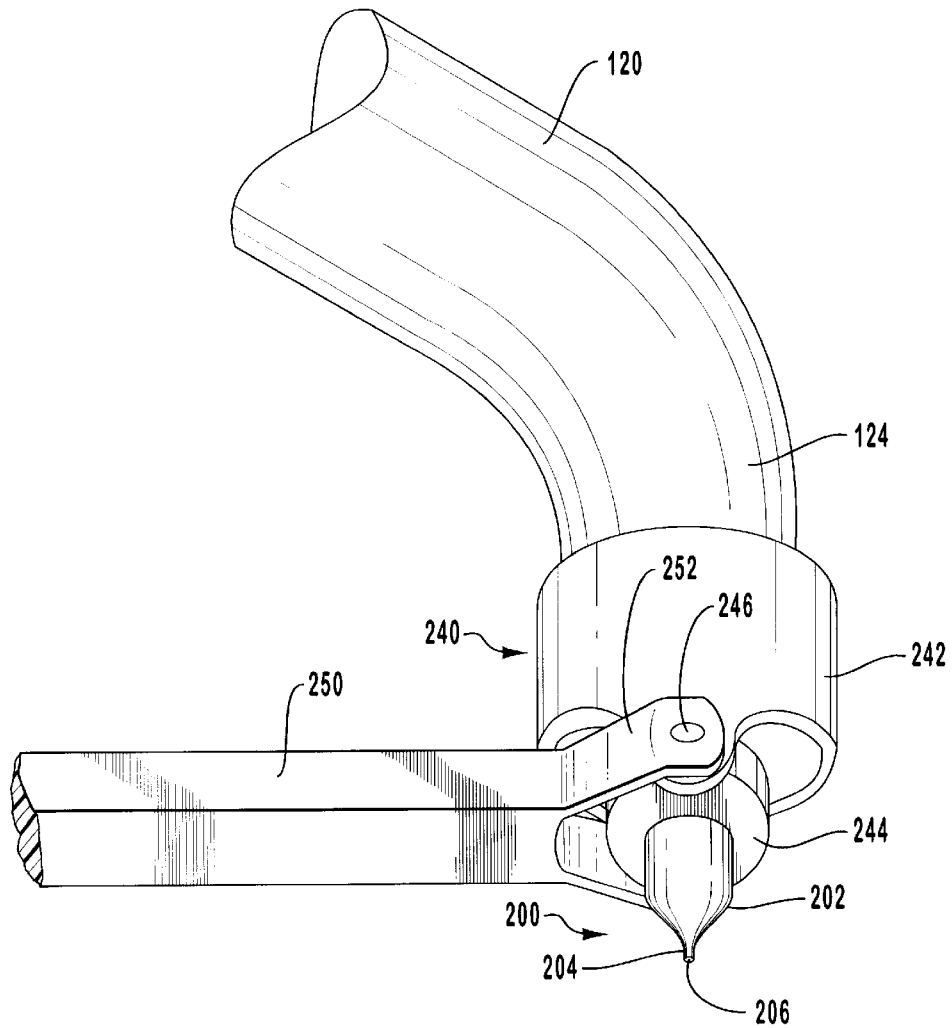
FIG. 18 is a perspective view of the fiber optic funnel shown in FIG. 14 pivotally coupled to a light guide in a similar fashion to that shown in FIG. 17, however, a handle is also provided.

A fiber optic funnel can also be pivotally coupled to a light guide as shown in FIGS. 17 and 18 via coupler 240. Coupler 240 comprises light guide collar 242 pivotally connected to a fiber optic funnel binding 244 via pins 246. Light guide collar 242 fits around transmission end 124 of light guide 120. The elliptical shape of binding 244 as shown in FIG. 17 enables easy pivoting, however, the binding may be circular or have any other easily pivoted configuration. Pins 246 may be an integral extension of binding 244 or separate components. Pins 246 move in the apertures of collar 242 as binding 244 and fiber optic funnel 200 are pivoted.

Embodiments configured to enable the fiber optic funnel to pivot preferably utilize a fiber optic funnel with a relatively short length to increase the ability of the funnel to pivot. Pivotal fiber optic funnels and couplers are also preferably configured to minimize the offset distance between the reception surface of the fiber optic funnel and the transmission end of the light guide. It is desirable to minimize the offset distance in order to minimize reflection by the reception surface of the fiber optic funnel. The reflectivity can however be minimized as discussed hereinabove through the use of antireflection coatings. Additionally, the reflectivity can be minimized through the use of a fiber optic funnel having a reception surface which is not flat but is curved or convex.

The components of coupler 240 can be designed to have a relatively close fit such that the fiber optic funnel remains pivoted after being positioned. In the embodiment shown in FIG. 18, the coupler is comprised as showed in FIG. 17, however, pins 246 also extend through the arms 252 of a handle 250. Handle 250 is adapted to being pivoted by the practioner as needed even while light is being transmitted through the instrument. This embodiment is particularly useful when polymerizing material in preparations located in teeth which are difficult to reach.

In an alternative embodiment of the handle, the pins are replaced by a portion of the handle or more specifically, an extension of the arms of the handle which are inserted through apertures 248 and into the collar. It may also be preferable to utilize a handle with elongated arms or a handle which is only connected at one side to the coupler such that the handle has a greater range of motion. In all of the embodiments of the handle, movement of handle 250 pivots binding 244.

Figure 19:
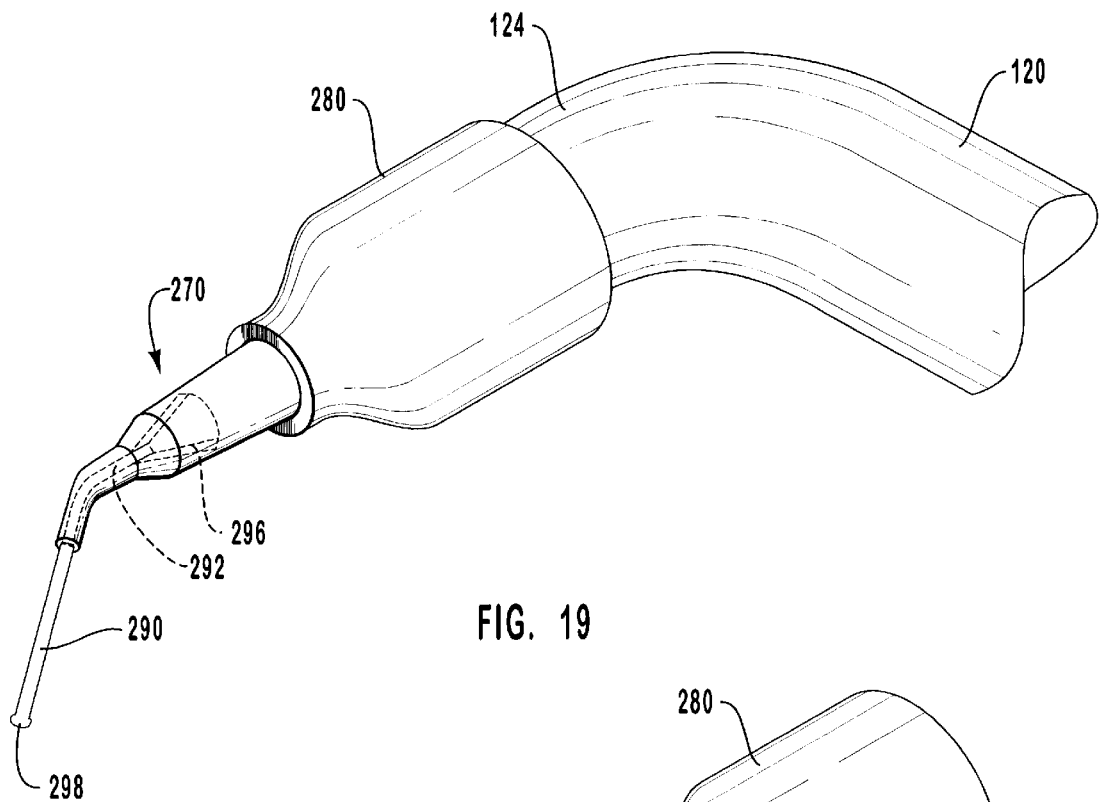
FIG. 19 is a perspective view with a hidden view depicting the use of another embodiment of a fiber optic funnel within a sheath tip having a monofiber and coupled to a light guide by another embodiment of a coupler.

Activation of hardenable material in deep and narrow preparations is best achieved through the use of instruments as shown in FIGS. 19–21. FIG. 19 depicts the assembled instrument with a hidden view while FIG. 20 is an exploded perspective view. A fiber optic funnel 260 is located within a sheath tip 270. More particularly, fiber optic funnel 260 is positioned within a chamber 276 of sheath tip, preferably in a mated configuration. Fiber optic funnel 260 and funnel end 272 of sheath tip 270 are coupled to transmission end 124 of light guide 120 by a coupler 280. Although, fiber optic funnel 260 is depicted in this embodiment, any suitable fiber optic funnel may be utilized.

A monofiber 290, which is preferably formed from plastic, extends through terminal end 274 of sheath tip 270 and into chamber 276. Monofiber 290 has a receiving end 292 and a terminal end 294. The receiving end may have the exact same configuration as the monofiber has along its length or the receiving end may be configured with receivers as shown in FIG. 19 at 296. Receivers 296 fit around transmission end 264 and in particular around apex 266. Receivers 296 protect fiber optic funnel 260 and may provide assistance in directing the light, particularly when apex 266 is larger than the inner diameter of monofiber 290. The terminal end may also have the exact same configuration as the monofiber has along its length or the terminal end may be configured with a bulbous terminus 298. Bulbous terminus 298 helps direct the light and enhances the ability of the monofiber to move within narrow and deep preparations. Monofiber 290 may have any suitable dimensions, however, the outer diameter is preferably in a range from about 0.1 mm to about 2 mm, and more preferably in a range from about 0.5 mm to about 1 mm.

FIG. 21 depicts a sheath tip 270 used in combination with a fiber optic funnel (not shown) as in the embodiments depicted in FIGS. 19 and 20. Sheath tip 270 and the fiber optic funnel are coupled to a transmission end 124 of light guide 120 by a coupler 240 as in the embodiments depicted in FIGS. 17 and 18. The terminal end of monofiber 290 is ensheathed by a protective tip 300 which is intended to be discarded after the completion of a dental procedure.

Figure 22A:
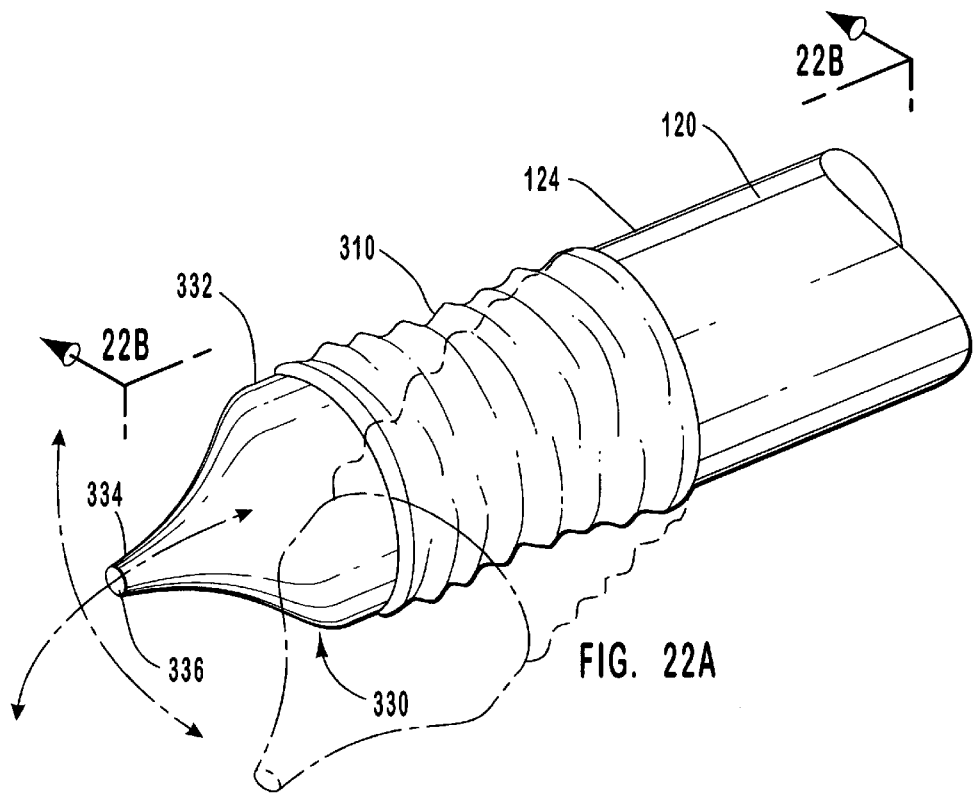
FIG. 22A is a perspective view of a fiber optic funnel pivotally coupled to a light guide with a sphere positioned between the fiber optic funnel and the light guide.
Figure 22B:
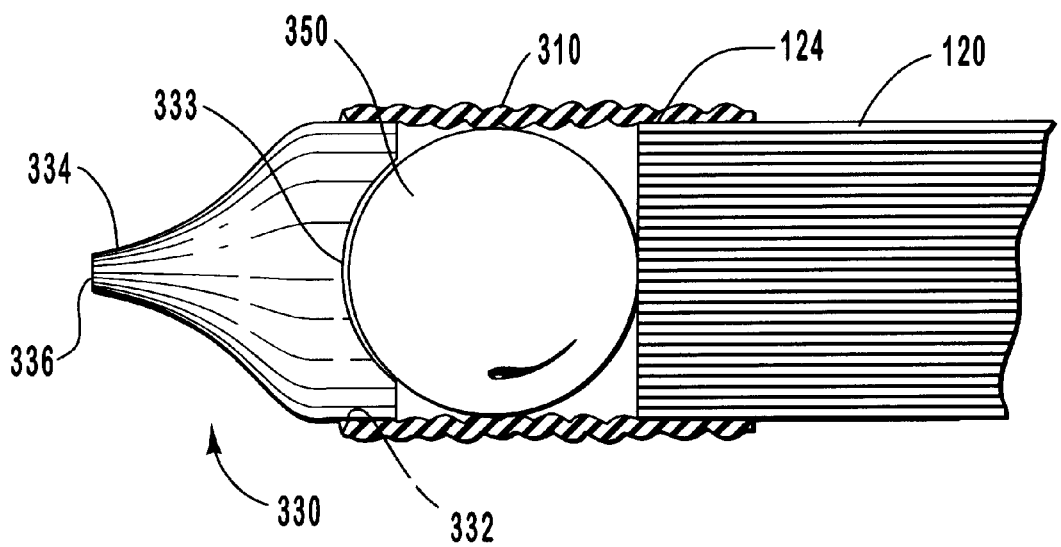
FIG. 22B is a cross-sectional view of the fiber optic funnel, sphere and light guide shown in FIG. 22A.
Figure 22C:
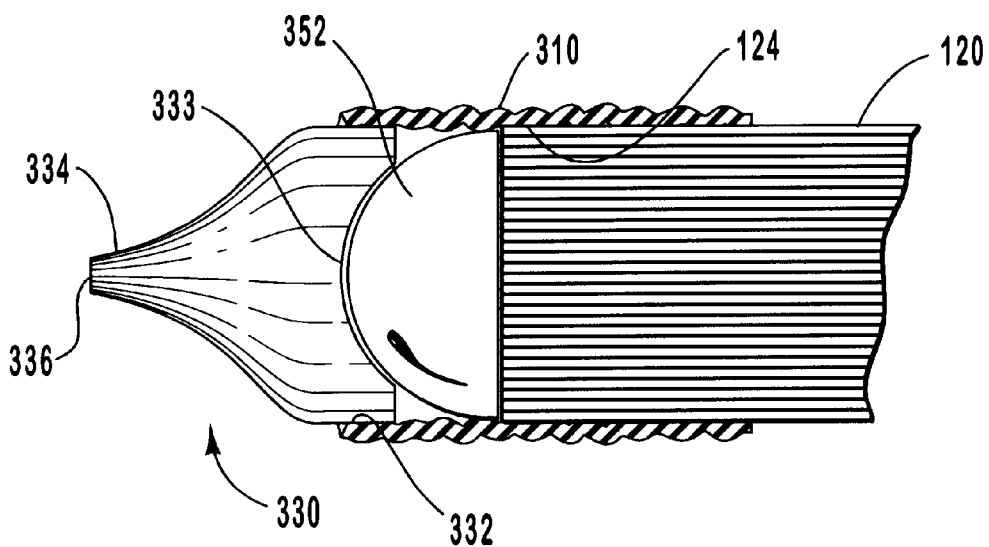
FIG. 22C is a cross-sectional view of the fiber optic funnel and light guide as shown in FIG. 22B, however, a hemisphere instead of a sphere is positioned between the fiber optic funnel and the light guide.

FIGS. 22A–B depicts another embodiment of the present invention which also enables a fiber optic funnel to be pivoted. FIG. 22B is a cross-section view of the embodiment shown in FIG. 22A. FIG. 22C depicts an embodiment of the invention which is similar to the embodiment shown in FIGS. 22A–B.

FIGS. 22A–C depict a unique coupler 310 which couples fiber optic funnel 330 to distal or transmission end 124 of light guide 120. Coupler 330 is ribbed in a configuration which enables coupler 330 to be pushed into a desired orientation and remain in the orientation until pushed again. Although, the embodiments shown in FIGS. 22A–C are shown with coupler 330, any of the couplers disclosed herein can also be used with the embodiments disclosed in relation to FIGS. 22A–C. Couplers used with the embodiments shown in FIGS. 22A–C, however preferably enable an angled position of a fiber optic funnel with respect to a light guide to be maintained, as does coupler 330.

FIG. 22B shows that a sphere 350 is positioned in coupler 310 between fiber optic funnel 330 and light guide 120. Light from light guide 120 passes through sphere 350 and into fiber optic funnel 330. An advantage of this embodiment is that light enters into fiber optic funnel 330 even when coupler 330 is bent as shown in FIG. 22A in phantom lines. Sphere 350 is preferably formed from glass.

FIG. 22C shows that in another embodiment a hemisphere 352 is disposed in coupler 310 between fiber optic funnel 330 and light guide 120. Hemisphere 352 acts essentially in the same manner as sphere 350 to receive light from light guide 120 and to transmit the light to fiber optic funnel 330 even when light guide 120, particularly transmission end 124, and fiber optic funnel 330 are not aligned on the same axis. Stated otherwise, sphere 350 and hemisphere 352 deliver or transfer light to fiber optic funnel 330 from light guide 120 even when fiber optic funnel 330 and light guide 120 are at an angle with respect to each other. Accordingly, sphere 350 and hemisphere 352 are examples of transfer means for transmitting light to a fiber optic funnel from a light guide even when the fiber optic funnel is positioned at an angle with respect to the light guide.

As in the other embodiments, fiber optic funnel 330 has a reception end 332 with a reception surface 333 opposite a conical transmission end 334 which terminates at an apex 336. However, in the embodiments shown in FIGS. 22A–C, reception surface 333 is shown in a concave configuration to receive the spherical surface of sphere 350 or hemisphere 352. Such a concave configuration of reception surface 333 is also useful in the other embodiments which enable the fiber optic funnel to be pivoted such as the embodiments shown in FIGS. 17–18. The reception surface of the fiber optic funnel is preferably concave when the fiber optic funnel is in a pivotable configuration and when the reception surface is offset from the transmission surface of the light guide by a distance of about 1 mm or greater.

In the embodiments shown in FIGS. 22A–C, reception end 332 and reception surface 333 of fiber optic funnel 330 have about the same diameter as transmission end 124 of light guide 120. The surfaces have about the same diameters to enable maximal light to be transmitted to the fiber optic funnel even when the fiber optic funnel has been angled with respect to the light guide. The other embodiments set forth herein, such as those discussed in relation to FIGS. 6, 11, 12–16, 19–20, generally have a fiber optic funnel with a reception surface having a smaller diameter than the transmission end of the light guide the. However, any embodiment disclosed herein may also be configured with a fiber optic funnel and a light guide which have opposing surfaces with approximately equal diameters.

In an alternative embodiment, any of the fiber optic funnels described above can also be utilized such that the fiber optic strands are more concentrated at the reception end 102 than at the transmission end 104. Stated otherwise, the orientation of the fiber optic funnel is reversed such that the fiber optic funnel has a reception end 102 with a larger diameter than the diameter of the transmission end.

In a preferred method of activating hardenable materials, the dental professional couples a radiant energy generating means to a reception end of a radiant energy guide means. Then, the user obtains a fiber optic funnel means and couples the reception end of the fiber optic funnel means to the transmission end of the radiant energy guide means via a coupling means. The user is then ready to position the fiber optic funnel means in a patient's mouth and aim the funnel at a hardenable material on a dental substrate. When the fiber optic funnel is in position, the light guide is activated to direct radiant energy from the radiant energy generating means through the guide means and the fiber optic funnel to the hardenable material.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A dental instrument for concentrating radiant energy that is delivered by a radiant energy guide means running from a means for generating the radiant energy, the instrument concentrating the radiant, energy at a desired region of one or more teeth of a patient, and comprising:

fiber optic funnel means for concentrating the radiant energy received from the guide means, the fiber optic funnel means comprising a plurality of fiber optic strands, the fiber optic funnel means having a reception end with a reception surface for receiving radiant energy from the guide means, the fiber optic funnel means having a transmission end opposite the reception end, the transmission end tapering to an apex such that the apex has a smaller diameter than the reception surface and being configured to enable light to be directed to a specific portion of a tooth, the fiber optic strands being oriented and configured such that radiant energy entering the reception surface is concentrated as it exits the apex of the transmission end, and separately removable coupling means for coupling the reception end of the fiber optic funnel means to the guide means.

2. An instrument as defined in claim 1, wherein the fiber optic funnel means is a fiber optic funnel.

3. An instrument as defined in claim 1, wherein the diameter of the apex of the fiber optic funnel is no greater than about ¾ of the diameter of the reception surface.

4. An instrument as defined in claim 1, wherein the transmission end of the fiber optic funnel means is generally conically shaped.

5. An instrument as defined in claim 1, wherein the apex is generally flat.

6. An instrument as defined in claim 1, wherein the apex is generally bulbous.

7. An instrument as defined in claim 1, wherein essentially all fiber strands terminate at the apex such that essentially all radiant energy entering the reception surface and transmitted via the strands exits the apex.

8. An instrument as defined in claim 1, wherein a portion of the fiber strands terminate at the apex while another portion of the fiber strands terminate along the transmission end such that some radiant energy entering the reception surface exits the apex and some radiant energy entering the reception surface exits along the transmission end.

9. An instrument as defined in claim 1, wherein portions of the fiber optic funnel means which neither receive or transmit radiant energy are covered with a protective sheath.

10. An instrument as defined in claim 1, wherein portions of the fiber optic funnel means which neither receive or transmit radiant energy are covered with a protective coating.

11. An instrument as defined in claim 1, wherein the reception surface of the fiber optic funnel means is coated with a material.

12. An instrument as defined in claim 1, wherein the fiber optic funnel means is located within a chamber of a sheath tip, wherein the sheath tip is coupled to the radiant energy guide means by the coupling means, and wherein a monofiber extends into the chamber to receive radiant energy from the apex of the fiber optic funnel means.

13. An instrument as defined in claim 1, wherein the fiber optic funnel means is located within a chamber of a sheath tip, wherein the sheath tip is coupled to the radiant energy guide means by the coupling means, wherein a receiving end of a monofiber extends into the chamber to receive radiant energy from the apex of the fiber optic funnel means and a terminal end of the monofiber extends out of sheath tip, and wherein a portion of the terminal end is ensheathed by a protective tip.

14. An instrument as defined in claim 1, wherein the coupling means is a coupler.

15. An instrument as defined in claim 1, wherein the coupling means is elastomeric.

16. An instrument as defined in claim 1, wherein the coupling means is relatively rigid.

17. An instrument as defined in claim 1, wherein the coupling means is capable of being coupled with radiant energy guide means having different diameters.

18. An instrument as defined in claim 1, wherein the coupling means enables the fiber optic funnel means to pivot.

19. An instrument as defined in claim 1, further comprising transfer means for transmitting radiant energy to the fiber optic funnel means from a radiant energy guide means even when the fiber optic funnel means is positioned at an angle with respect to the radiant energy guide means, wherein the transfer means is disposed within the coupling means.

20. A light concentration instrument for use with a means for generating light coupled to a dental light guide means for transmitting light from the light generating means, the instrument comprising:

a fiber optic funnel comprising a plurality of fiber optic strands, the fiber optic funnel having a reception end with a reception surface for receiving light from the dental light guide means, the fiber optic funnel having a transmission end opposite the reception end, the transmission end tapering to an apex such that the apex has a smaller diameter than the reception surface, the fiber optic strands being oriented and configured such that light entering the reception surface is concentrated as it exits the apex of the transmission end, and a separately removable coupler for coupling the reception end of the fiber optic funnel to the dental light guide means.

21. An instrument as defined in claim 20, wherein the diameter of the apex of the fiber optic funnel is no greater than about ¾ of the diameter of the reception surface.

22. An instrument as defined in claim 20, wherein the transmission end of the fiber optic funnel is generally conically shaped.

23. An instrument as defined in claim 20, wherein the transmission end and apex of the fiber optic funnel are configured to enable light to be directed to a specific portion of a tooth.

24. An instrument as defined in claim 20, wherein the apex is generally flat.

25. An instrument as defined in claim 20, wherein the apex is generally bulbous.

26. An instrument as defined in claim 20, wherein essentially all fiber strands terminate at the apex such that essentially all light entering the reception surface and transmitted via the strands exits the apex.

27. An instrument as defined in claim 20, wherein a portion of the fiber strands terminate at the apex while another portion of the fiber strands terminate along the transmission end such that some light entering the reception surface exits the apex and some light entering the reception surface exits along the transmission end.

28. An instrument as defined in claim 20, wherein portions of the fiber optic funnel which neither receive or transmit light are covered with a protective sheath.

29. An instrument as defined in claim 20, wherein portions of the fiber optic funnel which neither receive or transmit light are covered with a protective coating.

30. An instrument as defined in claim 20, wherein the reception surface of the fiber optic funnel is coated with a material.

31. An instrument as defined in claim 20, wherein the fiber optic funnel is located within a chamber of a sheath tip, wherein the sheath tip is coupled to the light guide means by the coupler, and wherein a monofiber extends into the chamber to receive light from the apex of the fiber optic funnel.

32. An instrument as defined in claim 20, wherein the fiber optic funnel is located within a chamber of a sheath tip, wherein the sheath tip is coupled to the light guide means by the coupler, wherein a receiving end of a monofiber extends into the chamber to receive light from the apex of the fiber optic funnel and a terminal end of the monofiber extends out of sheath tip, and wherein a portion of the terminal end is ensheathed by a protective tip.

33. An instrument as defined in claim 20, wherein the coupler is elastomeric.

34. An instrument as defined in claim 20, wherein the coupler is relatively rigid.

35. An instrument as defined in claim 20, wherein the coupler is capable of being coupled with light guide means having different diameters.

36. An instrument as defined in claim 20, wherein the coupler enables the fiber optic funnel to pivot.

37. An instrument as defined in claim 20, further comprising transfer means for transmitting light to the fiber optic funnel from a light guide means even when the fiber optic funnel is positioned at an angle with respect to the light guide means, wherein the transfer means is disposed within the coupler.

38. A dental instrument for concentrating radiant energy that is delivered by a radiant energy guide means running from a means for generating the radiant energy, the instrument concentrating the radiant energy at a desired region of one or more teeth of a patient, and comprising: p1 a fiber optic funnel means for concentrating radiant energy comprising a plurality of fiber optic strands, the fiber optic funnel having a reception end with a reception surface coated with a material for receiving light transmitted from the light guide means, the fiber optic funnel means having a transmission end opposite the reception end, the transmission end tapering to an apex such that the apex has a smaller diameter than the reception surface, the fiber optic strands being oriented and configured such that light entering the reception end is concentrated as it exits the apex of the transmission end, and a separately removable coupler for attaching the reception end of the fiber optic funnel means to the light guide means.

39. An instrument as defined in claim 38, wherein the fiber optic funnel means 16 is a fiber optic funnel.

40. An instrument as defined in claim 38, wherein the diameter of the apex of the fiber optic funnel is no greater than about ¾ of the diameter of the reception surface.

41. An instrument as defined in claim 38, wherein the transmission end of the fiber optic funnel means is generally conically shaped.

42. An instrument as defined in claim 38 wherein the transmission end and apex of the fiber optic funnel means are configured to enable light to be directed to a specific portion of a tooth.

43. An instrument as defined in claim 38, wherein the apex is generally flat.

44. An instrument as defined in claim 38, wherein the apex is generally bulbous.

45. An instrument as defined in claim 38, wherein essentially all fiber strands terminate at the apex such that essentially all light entering the reception surface and transmitted via the strands exits the apex.

46. An instrument as defined in claim 38, wherein a portion of the fiber strands terminate at the apex while another portion of the fiber strands terminate along the transmission end such that some light entering the reception surface exits the apex and some light entering the reception surface exits along the transmission end.

47. An instrument as defined in claim 38, wherein portions of the fiber optic funnel means which neither receive or transmit light are covered with a protective sheath.

48. An instrument as defined in claim 38, wherein portions of the fiber optic funnel means which neither receive or transmit light are covered with a protective coating.

49. An instrument as defined in claim 38, wherein the fiber optic funnel means is located within a chamber of a sheath tip, wherein the sheath tip is coupled to the light guide means by the coupling means, and wherein a monofiber extends into the chamber to receive light from the apex of the fiber optic funnel means.

50. An instrument as defined in claim 38, wherein the fiber optic funnel means is located within a chamber of a sheath tip, wherein the sheath tip is coupled to the light guide means by the coupling means, wherein a receiving end of a monofiber extends into the chamber to receive light from the apex of the fiber optic funnel means and a terminal end of the monofiber extends out of sheath tip, and wherein a portion of the terminal end is ensheathed by a protective tip.

51. An instrument as defined in claim 38, wherein the coupling means is a coupler.

52. An instrument as defined in claim 38, wherein the coupling means is elastomeric.

53. An instrument as defined in claim 38, wherein the coupling means is relatively rigid.

54. An instrument as defined in claim 38, wherein the coupling means is capable of being coupled with another light guide means having a different diameter.

55. An instrument as defined in claim 38, wherein the coupling means enables the fiber optic funnel means to pivot.

56. An instrument as defined in claim 38, further comprising transfer means for transmitting light to the fiber optic funnel means from the light guide means even when the fiber optic funnel means is positioned at an angle with respect to the light guide means, wherein the transfer means is disposed within the coupling means.

57. A method for directing concentrated radiant energy to a material on a dental substrate, comprising:

coupling a radiant energy generating means for generating radiant energy to a reception end of a radiant energy guide means for transmitting the radiant energy from the radiant energy generating means, the radiant energy guide means also having a transmission end;

obtaining a fiber optic funnel means for concentrating radiant energy, the fiber optic funnel means comprising a plurality of fiber optic strands, the fiber optic funnel means having a reception end with a reception surface, the fiber optic funnel means having a transmission end opposite the reception end, the transmission end tapering to an apex such that the apex has a smaller diameter than the reception surface, the fiber optic strands being oriented and configured such that radiant energy entering the reception end is concentrated as it exits the apex of the transmission end, coupling the reception end of the fiber optic funnel means to the transmission end of the radiant energy guide means via a coupling means for coupling the fiber optic funnel means to a radiant energy guide means such that the reception surface of the fiber optic funnel means may receive radiant energy from the transmission end of the radiant energy guide means; and directing the radiant energy, which was concentrated by the fiber optic funnel means after being received via the radiant energy guide means from the radiant energy generating means, to a material located on a dental substrate to initiate a chemical reaction.

\* \* \* \* \*

UNITED STATES PATENT AND TRADEMARK OFFICE
CERTIFICATE OF CORRECTION

PATENT NO.   : 6,208,788 B1
DATED        : March 27, 2001
INVENTOR(S)  : Vassiliy Nosov It is certified that error appears in the above-identified patent and that said Letters Patent is hereby corrected as shown below:

Column 1,
Line 44, after "angle" insert -- , --
Line 47, after "shape" insert -- . --

Column 3,
Line 47, change "in expensive" to -- inexpensive --
Line 62, change "concentrates" to -- concentrate --

Column 4,
Line 20, change "with" to -- without --
Line 49, change "with" to -- without --

Column 10,
Line 6, after "transmission" insert -- , --

Column 16,
Line 4, after "guide" delete "the"

Column 19,
Line 5, after "comprising:" delete "p1"
Line 27, after "38" insert -- , --

Signed and Sealed this

Sixteenth Day of April, 2002

Attest:

Attesting Officer

JAMES E. ROGAN
Director of the United States Patent and Trademark Office